United States Patent
Takahashi et al.

(10) Patent No.: US 10,793,520 B2
(45) Date of Patent: Oct. 6, 2020

(54) SULFONYLAMINOBENZAMIDE COMPOUND AND PEST CONTROL AGENT

(71) Applicant: Nippon Soda Co., Ltd., Chiyoda-ku, Tokyo (JP)

(72) Inventors: Jun Takahashi, Odawara (JP); Tetsuro Kato, Hiratsuka (JP); Takao Iwasa, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 16/316,710

(22) PCT Filed: Aug. 28, 2017

(86) PCT No.: PCT/JP2017/030739
§ 371 (c)(1),
(2) Date: Jan. 10, 2019

(87) PCT Pub. No.: WO2018/043400
PCT Pub. Date: Mar. 8, 2018

(65) Prior Publication Data
US 2019/0225577 A1    Jul. 25, 2019

(30) Foreign Application Priority Data
Aug. 30, 2016    (JP) .................... 2016-167859

(51) Int. Cl.
| C07C 311/09 | (2006.01) |
| A01N 41/06 | (2006.01) |
| A61P 33/00 | (2006.01) |
| A01N 43/40 | (2006.01) |
| C07D 277/28 | (2006.01) |
| A61P 33/14 | (2006.01) |
| A61K 31/426 | (2006.01) |
| C07D 213/74 | (2006.01) |
| A01N 43/653 | (2006.01) |
| A01N 43/78 | (2006.01) |
| C07D 277/44 | (2006.01) |
| A61K 31/44 | (2006.01) |
| A61K 31/16 | (2006.01) |
| C07C 303/40 | (2006.01) |
| C07C 303/36 | (2006.01) |

(52) U.S. Cl.
CPC ............ C07C 311/09 (2013.01); A01N 41/06 (2013.01); A01N 43/40 (2013.01); A01N 43/653 (2013.01); A01N 43/78 (2013.01); A61K 31/16 (2013.01); A61K 31/426 (2013.01); A61K 31/44 (2013.01); A61P 33/00 (2018.01); A61P 33/14 (2018.01); C07C 303/40 (2013.01); C07D 213/74 (2013.01); C07D 277/28 (2013.01); C07D 277/44 (2013.01); C07C 303/36 (2013.01)

(58) Field of Classification Search
None
See application file for complete search history.

(56) References Cited

U.S. PATENT DOCUMENTS

| 3,178,339 A * | 4/1965 | Frick ................. C07C 311/00 514/605 |
| 2004/0235959 A1 | 11/2004 | Lahm et al. |
| 2012/0058892 A1 | 3/2012 | Braun et al. |

FOREIGN PATENT DOCUMENTS

| EP | 0253310 A2 | 1/1988 |
| JP | 63-023868 A | 2/1988 |
| JP | 03-501020 A | 3/1991 |

(Continued)

OTHER PUBLICATIONS

International Search Report dated Oct. 31, 2017, in PCT/JP2017/030739, with English translation.
Duncia et al., "The Discovery of Potent Nonpeptide Angiotensin II Receptor Antagonists: A New Class of Potent Antihypertensives," J. Med. Chem., 1990, 33(5):1312-1329.
Lee et al., "2-Aminophenyl-1H-pyrazole as a Removable Directing Group for Copper-Mediated C—H Amidation and Sulfonamidation," Organic Letters, May 12, 2016, 18(11):2660-2663.
Shang et al., "Cu(II)-Mediated C—H Amidation and Amination of Arenes: Exceptional Compatibility with Heterocycles," Journal of the American Chemical Society, Feb. 17, 2014, 136(9):3354-3357.

(Continued)

*Primary Examiner* — Amy C Bonaparte
(74) *Attorney, Agent, or Firm* — Foley & Lardner LLP

(57) ABSTRACT

A compound represented by formula (I) or a salt thereof.

[Chemical formula 1]

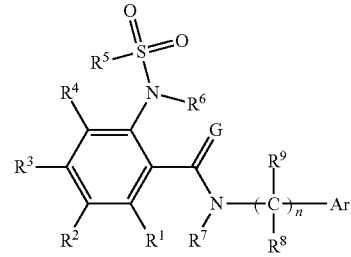

(I)

In formula (I), $R^1$ and $R^4$ each independently represent a hydrogen atom, or an unsubstituted or substituted C1 to C6 alkyl group or the like. $R^2$ represents a hydrogen atom, or an unsubstituted or substituted C1 to C6 alkyl group or the like. $R^3$ represents an unsubstituted or substituted C1 to C6 alkyl group or the like. $R^5$ represents a C1 to C6 haloalkyl group or the like. G represents an oxygen atom or a sulfur atom. $R^6$ and $R^7$ each independently represent a hydrogen atom, or an unsubstituted or substituted C1 to C6 alkyl group or the like. n represents 0 or 1. $R^8$ and $R^9$ each independently represent a hydrogen atom, or an unsubstituted or substituted C1 to C6 alkyl group. Ar represents an unsubstituted or substituted C6 to C10 aryl group or the like.

3 Claims, No Drawings

(56) References Cited

FOREIGN PATENT DOCUMENTS

| | | |
|---|---|---|
| JP | 2005-504084 A | 2/2005 |
| JP | 2013-536817 A | 9/2013 |
| WO | WO 89/06233 A1 | 7/1989 |
| WO | WO 00/78145 A1 | 12/2000 |
| WO | WO 01/05398 A1 | 1/2001 |
| WO | WO 01/87294 A1 | 11/2001 |
| WO | WO 2012/107475 A1 | 8/2012 |
| WO | WO 2015/195423 A1 | 12/2015 |
| WO | WO 2016/033341 A1 | 3/2016 |

OTHER PUBLICATIONS

Wen et al., "Discovery and Characterization of 2-(Cyclopropanesulfonamido)-N-(2-ethoxyphenyl)benzamide, ML382: a Potent and Selective Positive Allosteric Modulator of MrgX1," ChemMedChem, 2015, 10(1):57-61.

* cited by examiner

SULFONYLAMINOBENZAMIDE COMPOUND AND PEST CONTROL AGENT

TECHNICAL FIELD

The present invention relates to a sufonylaminobenzamide compound and a pest control agent. More specifically, the present invention relates to a sufonylaminobenzamide compound that has excellent insecticidal activity, miticidal activity and/or nematicidal activity, exhibits excellent safety, and can be synthesized favorably on an industrial scale, and also relates to a pest control agent that contains this compound as an active constituent.

CROSS-REFERENCE TO RELATED APPLICATIONS

The present application is the U.S. National Stage of PCT/JP2017/030739, filed Aug. 28, 2017, which claims priority on Japanese Patent Application No. 2016-167859, filed in Japan on Aug. 30, 2016, the content of which is incorporated herein by reference.

BACKGROUND ART

Many compounds having insecticidal, miticidal and/or nematicidal activity have been proposed. In order to enable these types of compounds to be used as agricultural chemicals, they must not only have sufficiently high potency, but must also be resistant to the development of drug resistance, cause no chemical damage to plants and no soil contamination, and exhibit low toxicity relative to domestic animals and fish and the like.

A compound represented by formula (A) is disclosed in Patent Document 1. Further, a compound represented by formula (B) is disclosed in Patent Document 2. According to Patent Document 1 and Patent Document 2, these compounds are apparently useful as parasiticides.

[Chemical formula 1]

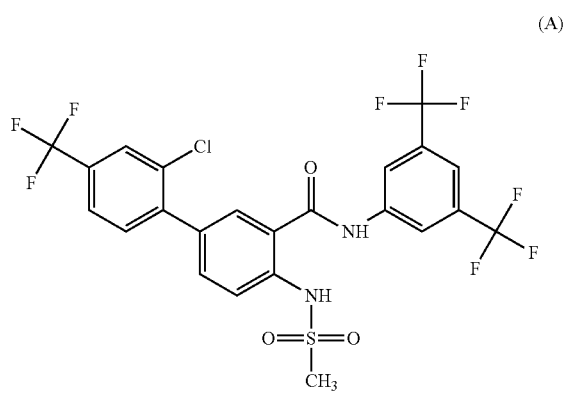

(A)

[Chemical formula 2]

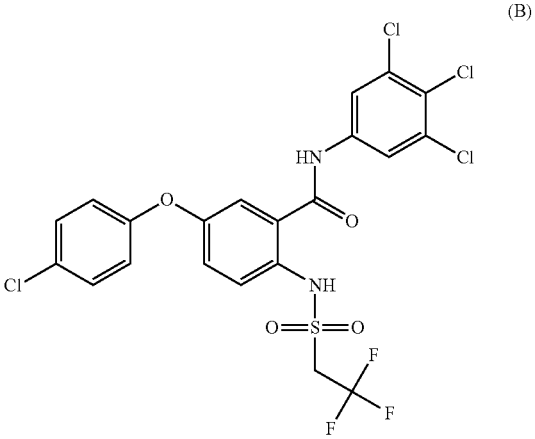

(B)

PRIOR ART LITERATURE

Patent Documents

Patent Document 1: WO 2015/195423 A1
Patent Document 2: WO 2016/033341 A1

SUMMARY OF THE INVENTION

Problems to be Solved by the Invention

Objects of the present invention are to provide a sufonylaminobenzamide compound that has pest control activity, and in particular, has excellent insecticidal, miticidal and/or nematicidal activity, exhibits excellent safety, and can be synthesized favorably on an industrial scale, and also to provide a pest control agent that contains this compound as an active constituent.

Means for Solving the Problems

As a result of intensive investigation aimed at achieving the above objects, the inventors were able to complete the present invention having the aspects described below.

[1] A compound represented by formula (I) or a salt thereof.

[Chemical formula 3]

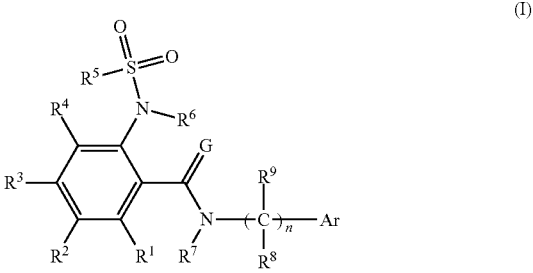

(I)

In formula (I),
$R^1$ and $R^4$ each independently represent a hydrogen atom, unsubstituted or substituted C1 to C6 alkyl group, halogeno group or cyano group.
$R^2$ represents a hydrogen atom, unsubstituted or substituted C1 to C6 alkyl group, unsubstituted or substituted C1 to C6 alkoxy group, halogeno group, cyano group, unsubstituted or substituted C1 to C6 alkylcarbonyl group, unsubstituted or substituted C1 to C6 alkoxycarbonyl group, unsubstituted or substituted C1 to C6 alkylthio group, unsubstituted or substituted C1 to C6 alkylsulfinyl group, unsubstituted or substituted C1 to C6 alkylsulfonyl group, group represented by —$NR^aR^b$, or group represented by —(C=O)—$NR^cR^d$.

$R^3$ represents an unsubstituted or substituted C1 to C6 alkyl group, unsubstituted or substituted C2 to C6 alkenyl group, unsubstituted or substituted C2 to C6 alkynyl group, hydroxyl group, unsubstituted or substituted C1 to C6 alkoxy group, formyl group, unsubstituted or substituted C1 to C6 alkylcarbonyl group, carboxyl group, unsubstituted or substituted C1 to C6 alkoxycarbonyl group, unsubstituted or substituted C1 to C6 alkylcarbonyloxy group, mercapto group, unsubstituted or substituted C1 to C6 alkylthio group, unsubstituted or substituted C1 to C6 alkylsulfinyl group, unsubstituted or substituted C1 to C6 alkylsulfonyl group, unsubstituted or substituted C3 to C8 cycloalkyl group, unsubstituted or substituted C6 to C10 aryl group, unsubstituted or substituted heteroaryl group, unsubstituted or substituted C6 to C10 aryloxy group, unsubstituted or substituted heteroaryloxy group, halogeno group, nitro group, cyano group, group represented by —$NR^aR^b$, group represented by —(C=O)—$NR^cR^d$, or group represented by —O—(C=O)—$NR^cR^d$.

$R^a$ and $R^b$ each independently represent a hydrogen atom, unsubstituted or substituted C1 to C6 alkyl group, unsubstituted or substituted C1 to C6 alkylcarbonyl group, or unsubstituted or substituted C1 to C6 alkoxycarbonyl group.

$R^c$ and $R^d$ each independently represent a hydrogen atom, or an unsubstituted or substituted C1 to C6 alkyl group.

$R^2$ and $R^3$ may be linked together to form, in combination with the carbon atoms to which they are bonded, an unsubstituted or substituted 5- or 6-membered ring.

$R^5$ represents a C1 to C6 haloalkyl group, C3 to C8 halocycloalkyl group, or C3 to C8 halocycloalkyl C1 to C6 alkyl group.

G represents an oxygen atom or a sulfur atom.

$R^6$ and $R^7$ each independently represent a hydrogen atom, unsubstituted or substituted C1 to C6 alkyl group, unsubstituted or substituted C1 to C6 alkylcarbonyl group, unsubstituted or substituted C1 to C6 alkoxycarbonyl group, unsubstituted or substituted C3 to C8 cycloalkyl group, unsubstituted or substituted C3 to C8 cycloalkylcarbonyl group, or unsubstituted or substituted C3 to C8 cycloalkoxycarbonyl group.

n represents 0 or 1.

$R^8$ and $R^9$ each independently represent a hydrogen atom, or an unsubstituted or substituted C1 to C6 alkyl group.

Ar represents an unsubstituted or substituted C6 to C10 aryl group or an unsubstituted or substituted 5- or 6-membered heteroaryl group.

[2] A pest control agent containing at least one substance selected from the group consisting of the compound disclosed above in [1] and salts thereof as an active constituent.

[3] An insecticide or miticide containing at least one substance selected from the group consisting of the compound disclosed above in [1] and salts thereof as an active constituent.

[4] A nematicide containing at least one substance selected from the group consisting of the compound disclosed above in [1] and salts thereof as an active constituent.

[5] An endoparasite control agent or parasiticide containing at least one substance selected from the group consisting of the compound disclosed above in [1] and salts thereof as an active constituent.

Effects of the Invention

The sufonylaminobenzamide compound of the present invention has pest control activity, and in particular, has excellent insecticidal, miticidal and/or nematicidal activity, exhibits excellent safety, and can be synthesized favorably on an industrial scale.

The pest control agent of the present invention can control pests that have a harmful effect on crops and pests that are problematic from a sanitation perspective. The pest control agent of the present invention exhibits an excellent control effect on agricultural pests even at low concentrations.

EMBODIMENTS FOR CARRYING OUT THE INVENTION

The sufonylamninobenzamide compound of the present invention is a compound represented by formula (I) (hereafter also referred to as the compound (I)) or a salt of the compound (1).

[Chemical formula 4]

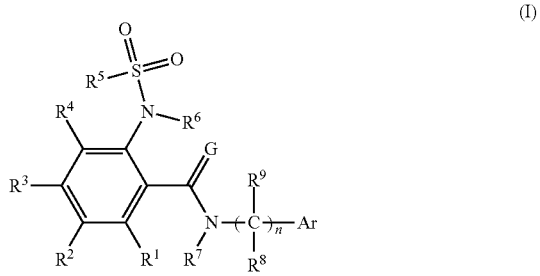

(I)

Firstly, in the present invention, the term "unsubstituted" means only the core group. When the term "substituted" does not appear and only the name of the core group is recorded, the meaning "unsubstituted" is implied unless specifically stated otherwise.

On the other hand, the term "substituted" means that one of the hydrogen atoms of the core group has been substituted with a group having a structure either the same as, or different from, the core group. Accordingly, the "substituent" is another group that is bonded to the core group. There may be either one substituent, or two or more substituents. In the case of two or more substituents, the substituents may be the same or different.

There are no particular limitations on the "substituent", provided it is chemically permissible and yields a compound having the effects of the present invention.

Specific examples of groups that can become a "substituent" include the groups listed below.

Halogeno groups such as a fluoro group, chloro group, bromo group, and iodo group;

C1 to C6 alkyl groups such as a methyl group, ethyl group, n-propyl group, i-propyl group, n-butyl group, s-butyl group, i-butyl group, t-butyl group, n-pentyl group, and n-hexyl group;

C2 to C6 alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group, and 5-hexenyl group;

C2 to C6 alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, and 1,1-dimethyl-2-butynyl group;

C3 to C8 cycloalkyl groups such as a cyclopropyl group, cyclobutyl group, cyclopentyl group, cyclohexyl group, cycloheptyl group, and cubanyl group;

C3 to C8 cycloalkenyl groups such as a 2-cyclopropenyl group, 2-cyclopentenyl group, 3-cyclohexenyl group, and 4-cyclooctenyl group;

C6 to C10 aryl groups such as a phenyl group and naphthyl group;

5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group, oxadiazolyl group, thiadiazolyl group, and tetrazolyl group;

6-membered heteroaryl groups such as a pyridyl group, pyrazinyl group, pyrimidinyl group, pyridazinyl group, and triazinyl group;

condensed ring heteroaryl groups such as an indolyl group, benzofuryl group, benzothienyl group, benzoimidazolyl group, benzoxazolyl group, benzothiazolyl group, quinolyl group, isoquinolyl group, and quinoxalinyl group;

cyclic ether groups such as an oxiranyl group, tetrahydrofuryl group, dioxolanyl group, and dioxanyl group;

cyclic amino groups such as an aziridinyl group, pyrrolidinyl group, piperidinyl group, piperazinyl group, and morpholinyl group;

a hydroxyl group; an oxo group;

C1 to C6 alkoxy groups such as a methoxy group, ethoxy group, n-propoxy group, i-propoxy group, n-butoxy group, s-butoxy group, i-butoxy group, and t-butoxy group;

C2 to C6 alkenyloxy groups such as a vinyloxy group, allyloxy group, propenyloxy group, and butenyloxy group;

C2 to C6 alkynyloxy groups such as an ethynyloxy group and propargyloxy group;

C6 to C10 aryloxy groups such as a phenoxy group and naphthoxy group;

5- to 6-membered ring heteroaryloxy groups such as a thiazolyloxy group and pyridyloxy group;

a carboxyl group;

C1 to C6 alkylcarbonyl groups such as a formyl group, acetyl group, and propionyl group;

C1 to C6 alkylcarbonyloxy groups such as a formyloxy group, acetyloxy group, and propionyloxy group;

C1 to C6 alkoxycarbonyl groups such as a methoxycarbonyl group, ethoxycarbonyl group, n-propoxycarbonyl group, i-propoxycarbonyl group, n-butoxycarbonyl group, and t-butoxycarbonyl group;

C1 to C6 haloalkyl groups such as a chloromethyl group, chloroethyl group, trifluoromethyl group, 1,2-dichloro-n-propyl group, 1-fluoro-n-butyl group, and perfluoro-n-pentyl group;

C2 to C6 haloalkenyl groups such as a 2-chloro-1-propenyl group and 2-fluoro-1-butenyl group;

C2 to C6 haloalkynyl groups such as a 4,4-dichloro-1-butynyl group, 4-fluoro-1-pentynyl group, and 5-bromo-2-pentynyl group;

C3 to C6 halocycloalkyl groups such as a 3,3-difluorocyclobutyl group;

C1 to C6 haloalkoxy groups such as a 2-chloro-n-propoxy group, 2,3-dichlorobutoxy group, trifluoromethoxy group, and 2,2,2-trifluoroethoxy group;

C2 to C6 haloalkenyloxy groups such as a 2-chloropropenyloxy group and 3-bromobutenyloxy group;

C1 to C6 haloalkylcarbonyl groups such as a chloroacetyl group, trifluoroacetyl group, and trichloroacetyl group;

a cyano group; a nitro group; an amino group;

C1 to C6 alkylamino groups such as a methylamino group, dimethylamino group, and diethylamino group;

C6 to C10 arylamino groups such as an anilino group and naphthylamino group;

C1 to C6 alkylcarbonylamino groups such as a formylamino group, acetylamino group, propanoylamino group, butyrylamino group, and i-propylcarbonylamino group;

C1 to C6 alkoxycarbonylanmino groups such as a methoxycarbonylamino group, ethoxycarbonylamino group, n-propoxycarbonylamino group, and i-propoxycarbonylamino group;

C1 to C6 alkylsulfoxyimino groups such as an S,S-dimethylsulfoxyimino group;

an aminocarbonyl group;

C1 to C6 alkylaminocarbonyl groups such as a methylaminocarbonyl group, dimethylaminocarbonyl group, ethylaminocarbonyl group, and i-propylaminocarbonyl group;

imino C1 to C6 alkyl groups such as an iminomethyl group, (1-imino)ethyl group, and (1-imino)-n-propyl group;

C1 to C6 alkoxyaminocarbonyl groups such as a methoxyaminocarbonyl group, ethoxyaminocarbonyl group, and i-propoxyaminocarbonyl group;

hydroxyimino C1 to C6 alkyl groups such as a hydroxyinminomethyl group, (1-hydroxyimino)ethyl group, and (1-hydroxyimino)propyl group;

C1 to C6 alkoxyimino C1 to C6 alkyl groups such as a methoxyiminomethyl group and (1-methoxyimino)ethyl group;

a mercapto group;

a pentafluorosulfanyl group;

C1 to C6 alkylthio groups such as a methylthio group, ethylthio group, n-propylthio group, i-propylthio group, n-butylthio group, i-butylthio group, s-butylthio group, and t-butylthio group;

C1 to C6 haloalkylthio groups such as a trifluoromethylthio group and 2,2,2-trifluoroethylthio group;

C2 to C6 alkenylthio groups such as a vinylthio group and allylthio group;

C2 to C6 alkynylthio groups such as an ethynylthio group and propargylthio group;

C1 to C6 alkylsulfinyl groups such as a methylsulfinyl group, ethylsulfinyl group, and t-butylsulfinyl group;

C1 to C6 haloalkylsulfinyl groups such as a trifluoromethylsulfinyl group and 2,2,2-trifluoroethylsulfinyl group;

C2 to C6 alkenylsulfinyl groups such as an allylsulfinyl group;

C2 to C6 alkynylsulfinyl groups such as a propargylsulfinyl group;

C1 to C6 alkylsulfonyl groups such as a methylsulfonyl group, ethylsulfonyl group, and t-butylsulfonyl group;

C1 to C6 haloalkylsulfonyl groups such as a trifluoromrethylsulfonyl group and 2,2,2-trifluoroethylsulfonyl group;

C2 to C6 alkenylsulfonyl groups such as an allylsulfonyl group;

C2 to C6 alkynylsulfonyl groups such as a propargylsulfonyl group;

tri C1 to C6 alkylsilyl groups such as a trimethylsilyl group, triethylsilyl group, and t-butyldimethylsilyl group; and tri C6 to C10 arylsilyl groups such as a triphenylsilyl group.

Further, in these "substituents", any of the hydrogen atoms in any of the above substituents may be substituted with a group of a different structure. Examples of the "substituents" in such cases include C1 to C6 alkyl groups, C1 to C6 haloalkyl groups, C1 to C6 alkoxy groups, C1 to C6 haloalkoxy groups, halogeno groups, a cyano group and a nitro group.

Terms such as "C1 to C6" indicate that the number of carbon atoms in the core group is from 1 to 6 or the like. This number of carbon atoms does not include the number of carbon atoms that exist within substituents. For example, in the case of an ethoxybutyl group, the core group is a butyl group and the ethoxy group is a substituent, and therefore this group is classified as a C2 alkoxy C4 alkyl group.

In formula (I), $R^1$ and $R^4$ each independently represent a hydrogen atom, unsubstituted or substituted C1 to C6 alkyl group, halogeno group or cyano group.

The "C1 to C6 alkyl group" for $R^1$ and $R^4$ may be linear or branched. Examples of the alkyl group include a methyl group, ethyl group, n-propyl group, n-butyl group, n-pentyl group, n-hexyl group, i-propyl group, i-butyl group, s-butyl group, t-butyl group, i-pentyl group, neopentyl group, 2-methylbutyl group, 2,2-dimethylbutyl group, and i-hexyl group.

Examples of preferred substituents on the "C1 to C6 alkyl group" of $R^1$ and $R^4$ include halogeno groups such as a fluoro group, chloro group, bromo group, and iodo group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, and trifluoromethoxy group; and a cyano group.

Examples of the halogeno group for $R^1$ and $R^4$ include a fluoro group, chloro group, bromo group, and iodo group.

$R^1$ and $R^4$ are preferably hydrogen atoms.

In formula (I), $R^2$ represents a hydrogen atom, unsubstituted or substituted C1 to C6 alkyl group, unsubstituted or substituted C1 to C6 alkoxy group, halogeno group, cyano group, unsubstituted or substituted C1 to C6 alkylcarbonyl group, unsubstituted or substituted C1 to C6 alkoxycarbonyl group, unsubstituted or substituted C1 to C6 alkylthio group, unsubstituted or substituted C1 to C6 alkylsulfinyl group, unsubstituted or substituted C1 to C6 alkylsulfonyl group, group represented by —$NR^aR^b$, or group represented by —(C=O)—$NR^cR^d$.

Examples of the "unsubstituted or substituted C1 to C6 alkyl group" and the "halogeno group" for $R^2$ include the same groups as those exemplified above for $R^1$ and $R^4$.

Examples of the "C1 to C6 alkoxy group" for $R^2$ include a methoxy group, ethoxy group, n-propoxy group, n-butoxy group, n-pentyloxy group, n-hexyloxy group, i-propoxy group, i-butoxy group, s-butoxy group, t-butoxy group, and i-hexyloxy group.

Examples of the "C1 to C6 alkylcarbonyl group" for $R^2$ include an acetyl group and propionyl group.

Examples of the "C1 to C6 alkoxycarbonyl group" for $R^2$ include a methoxycarbonyl group, ethoxycarbonyl group, n-propoxycarbonyl group, i-propoxycarbonyl group, and t-butoxycarbonyl group.

Examples of the "C1 to C6 alkylthio group" for $R^2$ include a methylthio group, ethylthio group, n-propylthio group, n-butylthio group, n-pentylthio group, n-hexylthio group, and i-propylthio group.

Examples of the "C1 to C6 alkylsulfinyl group" for $R^2$ include a methylsulfinyl group, ethylsulfinyl group, and t-butylsulfinyl group.

Examples of the "C1 to C6 alkylsulfonyl group" for $R^2$ include a methylsulfonyl group, ethylsulfonyl group, and t-butylsulfonyl group.

Examples of preferred substituents on the "C1 to C6 alkoxy group", "C1 to C6 alkylcarbonyl group", "C1 to C6 alkoxycarbonyl group", "C1 to C6 alkylthio group", "C1 to C6 alkylsulfinyl group" and "C1 to C6 alkylsulfonyl group" for $R^2$ include halogeno groups such as a fluoro group, chloro group, bromo group, and iodo group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, and trifluoromethoxy group; and a cyano group.

$R^a$ and $R^b$ in the "group represented by —$NR^aR^b$" for $R^2$ each independently represent a hydrogen atom, unsubstituted or substituted C1 to C6 alkyl group, unsubstituted or substituted C1 to C6 alkylcarbonyl group, or unsubstituted or substituted C1 to C6 alkoxycarbonyl group. Examples of the "C1 to C6 alkyl group" for $R^a$ and $R^b$ include the same groups as those exemplified above for $R^1$ and $R^4$. Examples of the "C1 to C6 alkylcarbonyl group" and the "C1 to C6 alkoxycarbonyl group" for $R^a$ and $R^b$ include the same groups as those exemplified above for $R^2$. Examples of preferred substituents on the "C1 to C6 alkyl group", "C1 to C6 alkylcarbonyl group" and "C1 to C6 alkoxycarbonyl group" for $R^a$ and $R^b$ include halogeno groups such as a fluoro group, chloro group, bromo group and iodo group, or a cyano group.

$R^c$ and $R^d$ in the "group represented by —(C=O)—$NR^cR^d$" for $R^2$ each independently represent a hydrogen atom, or an unsubstituted or substituted C1 to C6 alkyl group. Examples of the "unsubstituted or substituted C1 to C6 alkyl group" for $R^c$ and $R^d$ include the same groups as those exemplified above for $R^a$ and $R^b$.

$R^2$ is preferably a hydrogen atom, unsubstituted or substituted C1 to C6 alkyl group (and preferably a substituted C1 to C6 alkyl group), or halogeno group.

In formula (I), $R^3$ represents an unsubstituted or substituted C1 to C6 alkyl group, unsubstituted or substituted C2 to C6 alkenyl group, unsubstituted or substituted C2 to C6 alkynyl group, hydroxyl group, unsubstituted or substituted C1 to C6 alkoxy group, formyl group, unsubstituted or substituted C1 to C6 alkylcarbonyl group, carboxyl group, unsubstituted or substituted C1 to C6 alkoxycarbonyl group, unsubstituted or substituted C1 to C6 alkylcarbonyloxy group, mercapto group, unsubstituted or substituted C1 to C6 alkylthio group, unsubstituted or substituted C1 to C6 alkylsulfinyl group, unsubstituted or substituted C1 to C6 alkylsulfonyl group, unsubstituted or substituted C3 to C8 cycloalkyl group, unsubstituted or substituted C6 to C10 aryl group, unsubstituted or substituted heteroaryl group, unsubstituted or substituted C6 to C10 aryloxy group, unsubstituted or substituted heteroaryloxy group, halogeno group, nitro group, cyano group, group represented by —$NR^aR^b$, group represented by —(C=O)—$NR^cR^d$, or group represented by —O—(C=O)—$NR^cR^d$.

Examples of the "unsubstituted or substituted C1 to C6 alkyl group" and the "halogeno group" for $R^3$ include the same groups as those exemplified above for $R^1$ and $R^4$.

Examples of the "unsubstituted or substituted C1 to C6 alkoxy group", "unsubstituted or substituted C1 to C6 alkylcarbonyl group", "unsubstituted or substituted C1 to C6 alkoxycarbonyl group", "unsubstituted or substituted C1 to C6 alkylthio group", "unsubstituted or substituted C1 to C6 alkylsulfinyl group" and "unsubstituted or substituted C1 to C6 alkylsulfonyl group" for $R^3$ include the same groups as those exemplified above for $R^2$.

Examples of the "C2 to C6 alkenyl group" for $R^3$ include a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group and 5-hexenyl group.

Examples of the "C2 to C6 alkynyl group" for $R^3$ include an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group, and 1,1-dimethyl-2-butynyl group.

Examples of the "C1 to C6 alkylcarbonyloxy group" for $R^3$ include an acetyloxy group, propionyloxy group, and butyryloxy group.

Examples of preferred substituents on the "C2 to C6 alkenyl group", "C2 to C6 alkynyl group" and "C1 to C6 alkylcarbonyloxy group" for $R^3$ include halogeno groups such as a fluoro group, chloro group, bromo group, and iodo group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, and trifluoromethoxy group; and a cyano group.

Examples of the "C3 to C8 cycloalkyl group" for $R^3$ include a cyclopropyl group, cyclobutyl group, cyclopentyl group, cyclohexyl group, and cycloheptyl group.

The "C6 to C10 aryl group" for $R^3$ may be a monocyclic aryl group or a polycyclic aryl group. In a polycyclic group, provided at least one ring is an aromatic ring, each remaining ring may be a saturated alicyclic ring, unsaturated alicyclic ring or aromatic ring.

Examples of the "C6 to C10 aryl group" include a phenyl group, naphthyl group, azulenyl group, indenyl group, indanyl group, and tetralinyl group.

Examples of the "heteroaryl group" for $R^3$ include 5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group (and specifically, a [1,2,3]-triazolyl group or [1,2,4]-triazolyl group), oxadiazolyl group (and specifically, a [1,2,3]-oxadiazolyl group, [1,2,4]-oxadiazolyl group, [1,2,5]-oxadiazolyl group or [1,3,4]-oxadiazolyl group), thiadiazolyl group, and tetrazolyl group; 6-membered heteroaryl groups such as a pyridyl group, pyrazinyl group, pyrimidinyl group, pyridazinyl group, and triazinyl group; and condensed ring heteroaryl groups such as an indolyl group, benzofuryl group, benzothienyl group, benzoimidazolyl group, benzoxazolyl group, benzothiazolyl group, quinolyl group, isoquinolyl group, and quinoxalinyl group.

Examples of the "C6 to C10 aryloxy group" for $R^3$ include a phenoxy group, naphthyloxy group, azulenyloxy group, indenyloxy group, indanyloxy group, and tetralinyloxy group.

Examples of the "heteroaryloxy group" for $R^3$ include 5- and 6-membered heteroaryloxy groups such as a thiazolyloxy group and pyridyloxy group.

Examples of preferred substituents on the "C3 to C8 cycloalkyl group", "C6 to C10 aryl group", "heteroaryl group", "C6 to C10 aryloxy group" and "heteroaryloxy group" for $R^3$ include halogeno groups such as a fluoro group, chloro group, bromo group, and iodo group; C1 to C6 alkyl groups such as a methyl group, ethyl group, n-propyl group, i-propyl group, n-butyl group, s-butyl group, i-butyl group, t-butyl group, n-pentyl group, and n-hexyl group; C1 to C6 haloalkyl groups such as a chloromethyl group, chloroethyl group, trifluoromethyl group, pentafluoroethyl group, 1,2-dichloro-n-propyl group, 1,1,1,3,3,3-hexafluoropropan-2-yl group, perfluoropropan-2-yl group, 1-fluoro-n-butyl group, and perfluoro-n-pentyl group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, and trifluoromethoxy group; a cyano group; and a pentafluorosulfanyl group, and examples of particularly preferred substituents include halogeno groups such as a fluoro group, chloro group, bromo group, and iodo group; and C1 to C6 haloalkyl groups such as a chloromethyl group, chloroethyl group, trifluoromethyl group, pentafluoroethyl group, 1,2-dichloro-n-propyl group, 1,1,1,3,3,3-hexafluoropropan-2-yl group, perfluoropropan-2-yl group, 1-fluoro-n-butyl group, and perfluoro-n-pentyl group.

$R^a$ and $R^b$ in the "group represented by —$NR^aR^b$" for $R^3$ each independently represent a hydrogen atom, unsubstituted or substituted C1 to C6 alkyl group, unsubstituted or substituted C1 to C6 alkylcarbonyl group, or unsubstituted or substituted C1 to C6 alkoxycarbonyl group.

Examples of the "unsubstituted or substituted C1 to C6 alkyl group", "unsubstituted or substituted C1 to C6 alkylcarbonyl group" and "unsubstituted or substituted C1 to C6 alkoxycarbonyl group" for $R^a$ and $R^b$ in the "group represented by —$NR^aR^b$" for $R^3$ include the same groups as those exemplified above for $R^a$ and $R^b$ in the "group represented by —$NR^aR^b$" for $R^2$.

$R^c$ and $R^d$ in the "group represented by —(C=O)—$NR^cR^d$" and the "group represented by —O—(C=O)—$NR^cR^d$" for $R^3$ each independently represent a hydrogen atom, or an unsubstituted or substituted C1 to C6 alkyl group. Examples of the "unsubstituted or substituted C1 to C6 alkyl group" for $R^c$ and $R^d$ in the "group represented by —(C=O)—$NR^cR^d$" and the "group represented by —O—(C=O)—$NR^cR^d$" for $R^3$ include the same groups as those exemplified above for $R^c$ and $R^d$ in the "group represented by —(C=O)—$NR^cR^d$" for $R^2$.

$R^3$ is preferably an unsubstituted or substituted C1 to C6 alkyl group, unsubstituted or substituted C1 to C6 alkoxy group (and preferably a substituted C1 to C6 alkoxy group), unsubstituted or substituted C6 to C10 aryl group (and preferably an unsubstituted or substituted phenyl group), unsubstituted or substituted heteroaryl group (and preferably an unsubstituted or substituted 5- or 6-membered heteroaryl group), halogeno group, nitro group, or cyano group.

The "5- or 6-membered heteroaryl group" for $R^3$ is preferably a triazolyl group or pyridyl group.

In formula (I), $R^2$ and $R^3$ may be linked together to form, in combination with the carbon atoms to which they are bonded, an unsubstituted or substituted 5- or 6-membered ring.

Examples of the 5- or 6-membered ring formed by $R^2$, $R^3$ and the carbon atoms to which they are bonded include 1,3-dioxolane, tetrahydrofuran, piperidine, piperazine, morpholine, 1,4-oxathiane, 1,4-oxathiane, 4,4-dioxide, thiomorpholine, cyclohexane, piperidin-2-one, thiomorpholin-3-one, and cyclohexanone. Examples of preferred substituents on the 5- or 6-membered ring include halogeno groups.

In formula (I), $R^5$ represents a C1 to C6 haloalkyl group, C3 to C8 halocycloalkyl group, or C3 to C8 halocycloalkyl C1 to C6 alkyl group.

Examples of the "C1 to C6 haloalkyl group" for $R^5$ include a fluoromethyl group, chloromethyl group, bromomethyl group, iodomethyl group, difluoromethyl group, dichloromethyl group, trifluoromethyl group, chlorodifluoromethyl group, trichloromethyl group, bromodifluoromethyl group, 2-fluoroethyl group, 2-chloroethyl group, 2-bromoethyl group, 2,2-difluoroethyl group, 2,2,2-trifluoroethyl group, 2-chloro-2,2-difluoroethyl group, 2,2,2-trichloroethyl group, 1,1,2,2-tetrafluoroethyl group, 2-chloro-1,1,2-trifluoroethyl group, pentafluoroethyl group, 3,3,3-trifluoropropyl group, 2,2,3,3,3-pentafluoropropyl group, 1,1,2,3,3,3-hexafluoropropyl group, heptafluoropropyl group, 2,2,2-trifluoro-1-(trifluoromethyl)ethyl group, 1,2,2,2-tetrafluoro-1-(trifluoromethyl)ethyl group, 2,2,3,3,4,4,4-heptafluorobutyl group, and nonafluorobutyl group.

Examples of the "C3 to C8 halocycloalkyl group" for $R^5$ include a 1-fluorocyclopropyl group, 2-fluorocyclopropyl group, 1-chlorocyclopropyl group, 2-chlorocyclopropyl group, 2,2-difluorocyclopropyl group, 2,2-dichlorocyclopropyl group, 2,2,3,3-tetrafluorocyclopropyl group, 2-fluorocyclopentyl group, 3-fluorocyclopentyl group, 2-chlorocyclopentyl group, 3-chlorocyclopentyl group, 3,4-difluorocyclohexyl group, 3,4-dichlorocyclohexyl group, and 3,4-dibromocyclohexyl group.

Examples of the "C3 to C8 halocycloalkyl C1 to C6 alkyl group" for $R^5$ include a 2-fluorocyclopropylmethyl group, 1-fluorocyclopropylmethyl group, 1,2-difluorocyclopropylmethyl group, and 2,2,3,3-tetrafluorocyclopropylmethyl group.

$R^5$ is preferably a C1 to C6 haloalkyl group, and more preferably a C1 to C4 haloalkyl group.

In formula (I), G represents an oxygen atom or a sulfur atom.

G is preferably an oxygen atom.

In formula (I), $R^6$ and $R^7$ each independently represent a hydrogen atom, unsubstituted or substituted C1 to C6 alkyl group, unsubstituted or substituted C1 to C6 alkylcarbonyl group, unsubstituted or substituted C1 to C6 alkoxycarbonyl group, unsubstituted or substituted C3 to C8 cycloalkyl group, unsubstituted or substituted C3 to C8 cycloalkylcarbonyl group, or unsubstituted or substituted C3 to C8 cycloalkoxycarbonyl group.

Examples of the "unsubstituted or substituted C1 to C6 alkyl group" for $R^6$ and $R^7$ include the same groups as those exemplified above for $R^1$ and $R^4$.

Examples of the "unsubstituted or substituted C1 to C6 alkylcarbonyl group", "unsubstituted or substituted C1 to C6 alkoxycarbonyl group" and "unsubstituted or substituted C3 to C8 cycloalkyl group" for $R^6$ and $R^7$ include the same groups as those exemplified above for $R^3$.

Examples of the "C3 to C8 cycloalkylcarbonyl group" for $R^6$ and $R^7$ include a cyclopropanecarbonyl group, cyclopentanecarbonyl group, and cyclohexanecarbonyl group.

Examples of the "C3 to C8 cycloalkoxycarbonyl group" for $R^6$ and $R^7$ include a cyclopropoxycarbonyl group, cyclopentyloxycarbonyl group, and cyclohexyloxycarbonyl group.

Examples of preferred substituents on the "C3 to C8 cycloalkylcarbonyl group" and "C3 to C8 cycloalkoxycarbonyl group" for $R^6$ and $R^7$ include halogeno groups such as a fluoro group, chloro group, bromo group, and iodo group; C1 to C6 alkyl groups such as a methyl group, ethyl group, n-propyl group, i-propyl group, n-butyl group, s-butyl group, i-butyl group, t-butyl group, n-pentyl group, and n-hexyl group; C1 to C6 haloalkyl groups such as a chloromethyl group, chloroethyl group, trifluoromethyl group, 1,2-dichloro-n-propyl group, 1-fluoro-n-butyl group, and perfluoro-n-pentyl group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, and trifluoromethoxy group; and a cyano group.

Each of $R^6$ and $R^7$ is preferably a hydrogen atom or an unsubstituted or substituted C1 to C6 alkyl group (and preferably an unsubstituted C1 to C6 alkyl group), and is more preferably a hydrogen atom.

In formula (I), n indicates the number of divalent groups represented by $CR^8R^9$ shown inside the brackets, and is 0 or 1.

In formula (I), $R^8$ and $R^9$ each independently represent a hydrogen atom, or an unsubstituted or substituted C1 to C6 alkyl group (and preferably an unsubstituted C1 to C6 alkyl group).

Examples of the "unsubstituted or substituted C1 to C6 alkyl group" for $R^8$ and $R^9$ include the same groups as those exemplified above for $R^1$ and $R^4$.

In formula (I), Ar represents an unsubstituted or substituted C6 to C10 aryl group or an unsubstituted or substituted 5- or 6-membered heteroaryl group.

Examples of the "C6 to C10 aryl group" for Ar include the same groups as those exemplified above for $R^3$.

Examples of the "5- or 6-membered heteroaryl group" for Ar include 5-membered heteroaryl groups such as a pyrrolyl group, furyl group, thienyl group, imidazolyl group, pyrazolyl group, oxazolyl group, isoxazolyl group, thiazolyl group, isothiazolyl group, triazolyl group (and specifically, a [1,2,3]-triazolyl group or [1,2,4]-triazolyl group), oxadiazolyl group (and specifically, a [1,2,3]-oxadiazolyl group, [1,2,4]-oxadiazolyl group, [1,2,5]-oxadiazolyl group or [1,3,4]-oxadiazolyl group), thiadiazolyl group, and tetrazolyl group; and 6-membered heteroaryl groups such as a pyridyl group, pyrazinyl group, pyrimidinyl group, pyridazinyl group, and triazinyl group.

Examples of preferred substituents on the "C6 to C10 aryl group" and "5- or 6-membered heteroaryl group" for Ar include halogeno groups such as a fluoro group, chloro group, bromo group, and iodo group; C1 to C6 alkyl groups such as a methyl group, ethyl group, n-propyl group, i-propyl group, n-butyl group, s-butyl group, i-butyl group, t-butyl group, n-pentyl group, and n-hexyl group; C1 to C6 haloalkyl groups such as a chloromethyl group, chloroethyl group, trifluoromethyl group, pentafluoroethyl group, 1,2-dichloro-n-propyl group, 1,1,1,3,3,3-hexafluoropropan-2-yl group, perfluoropropan-2-yl group, 1-fluoro-n-butyl group, and perfluoro-n-pentyl group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, trifluoromethoxy group, and 2,2,2-trifluoroethoxy group; a carboxyl group; C1 to C6 alkylcarbonyl groups such as an acetyl group and propionyl group; C1 to C6 alkylcarbonylamino groups such as an acetylamino group, propanoylamino group, butyrylamino group, and i-propylcarbonylamino group; C1 to C6 alkoxycarbonyl groups such as a methoxycarbonyl group, ethoxycarbonyl group, n-propoxycarbonyl group, i-propoxycarbonyl group, n-butoxycarbonyl group, and t-butoxycarbonyl group; C1 to C6 alkylaminocarbonyl groups such as a methylaminocarbonyl group, dimethylaminocarbonyl group, ethylaminocarbonyl group, and i-propylaminocarbonyl group; C1 to C6 haloalkylthio groups such as a trifluoromethylthio group; alkylsulfonyl groups such as a methylsulfonyl group; unsubstituted or C1 to C6 alkyl-substituted 5-membered heteroaryl groups such as a triazolyl group, oxadiazolyl group, pyrazolyl group, 3-methyl-1,2,4-oxazol-5-yl group, and 5-methyl-1,3,4-oxazol-5-yl group; a 4,5-dihydrooxazol-2-yl group; 6-membered heteroaryl groups such as a pyridyl group; C1 to C6 alkoxyimino C1 to C6 alkyl groups such as a methoxyiminomethyl group and (1-methoxyimino)ethyl group; a cyano group; a nitro group; and a pentafluorosulfanyl group.

Examples of particularly preferred substituents on the "C6 to C10 aryl group" and "5- or 6-membered heteroaryl group" for Ar include halogeno groups such as a fluoro group, chloro group, bromo group, and iodo group; C1 to C6 alkyl groups such as a methyl group, ethyl group, n-propyl group, i-propyl group, n-butyl group, s-butyl group, i-butyl group, t-butyl group, n-pentyl group, and n-hexyl group; C1 to C6 haloalkyl groups such as a chloromethyl group, chloroethyl group, trifluoromethyl group, pentafluoroethyl group, 1,2-dichloro-n-propyl group, 1,1,1,3,3,3-hexafluoropropan-2-yl group, perfluoropropan-2-yl group, 1-fluoro-n-butyl group, and perfluoro-n-pentyl group; C1 to C6 alkoxy groups such as a methoxy group, ethoxy group, n-propoxy group, i-propoxy group, n-butoxy group, s-butoxy group, i-butoxy group, and t-butoxy group; C1 to C6 haloalkoxy groups such as a 2-chloro-n-propoxy group, 2,3-dichlorobutoxy group, trifluoromethoxy group, and 2,2,2-trifluoroethoxy group; a carboxyl group; C1 to C6 alkylcarbonyl groups such as an acetyl group and propionyl group; C1 to C6 alkoxycarbonyl groups such as a methoxycarbonyl group, ethoxycarbonyl group, n-propoxycarbonyl group, i-propoxycarbonyl group, n-butoxycarbonyl group, and t-butoxycarbonyl group; unsubstituted or C1 to C6 alkyl-substituted 5-membered heteroaryl groups such as a triazolyl group, oxadiazolyl group, pyrazolyl group, 3-methyl-1,2,4-oxazol-5-yl group, and 5-methyl-1,3,4-oxazol-5-yl group; a 4,5-dihydrooxazol-2-yl group; 6-membered heteroaryl groups such as a pyridyl group; C1 to C6 alkoxyimino C1 to C6 alkyl groups such as a methoxyiminomethyl group and (1-methoxyimino)ethyl group; a cyano group; a nitro group; and a pentafluorosulfanyl group.

Ar is preferably an unsubstituted or substituted phenyl group, an unsubstituted or substituted thiazolyl group, or an unsubstituted or substituted pyridyl group, and is more preferably a substituted phenyl group, a substituted thiazolyl group, or a substituted pyridyl group.

There are no particular limitations on the salt of the compound (I), provided the salt is an agriculturally and horticulturally acceptable salt. Examples include salts of inorganic acids such as hydrochloric acid and sulfuric acid; salts of organic acids such as acetic acid and lactic acid; salts of alkali metals such as lithium, sodium and potassium; salts of alkaline earth metals such as calcium and magnesium; salts of transition metals such as iron and copper; and salts of organic bases such as ammonia, triethylamine, tributylamine, pyridine and hydrazine.

The compound (I) or the salt of the compound (I) is not particularly limited by the production method used. Further, the salt of the compound (I) can be obtained from the compound (I) by conventional methods. The compound (I) of the present invention or the salt of the compound (I) can be obtained by conventional production methods. Examples of the production method for the compound (I) of the present invention or the salt of the compound (I) include the methods described in the examples.

The sufonylaminobenzamide compound of the present invention has an excellent control effect on pests such as various agricultural pests, mites and nematodes that affect the growth of plants.

Further, because the sufonylaminobenzamide compound of the present invention causes no chemical damage to crops and exhibits low toxicity to fish and warm-blooded animals, it is a very safe compound. Accordingly, the compound is useful as an active constituent for insecticides, miticides and nematicides.

Moreover, in recent years, many insect pests such as Plutellidae, Delphacidae, Cicadellidae and Aphididae have developed resistance to various known chemical agents, causing problems of inadequate potency for these chemical agents, and there is much demand for a chemical agent that is also effective against these resistant strains. The sufonylaminobenzamide compound of the present invention exhibits an excellent control effect against insect pests, not only sensitive strains but also various resistant strains, and against mites of miticide-resistant strains.

Furthermore, the sufonylaminobenzamide compound of the present invention exhibits efficacy against all growth stages of the control target organisms, and for example exhibits a control effect on the eggs, nymphs, larvae, pupae and adults of mites, insects and nematodes.

[Pest Control Agent, Insecticide, Miticide, or Nematicide]

The pest control agent, or insecticide, miticide or nematicide, of the present invention contains at least one compound selected from the sufonylaminobenzamide compounds of the present invention as an active constituent. There are no particular limitations on the amount of the sufonylaminobenzamide compound of the present invention contained within the pest control agent, insecticide, miticide or nematicide of the present invention, provided a pest control effect is exhibited.

The pest control agent, or insecticide, miticide or nematicide, of the present invention is preferably used on plants such as grains; vegetables; root vegetables; tubers; flowers and ornamental plants; fruit trees; trees such as foliage plants, tea plants, coffee plants, and cacao plants; pasture grasses; lawn grasses; and cotton plants.

During application to the plant, the pest control agent, insecticide, miticide or nematicide of the present invention may be applied to any portion of the plant, including the leaves, stems, stalks, flowers, buds, fruit, seeds, sprouts, roots, tubers, tuberous roots, shoots or cuttings.

Furthermore, the pest control agent, or insecticide, miticide or nematicide, of the present invention is not particularly limited in terms of the types of plants on which it can be applied. Examples of the types of plants include original species, variants, improved varieties, cultivars, mutants, hybrids, and genetically modified species (GMO).

The pest control agent of the present invention can be used for a seed treatment, foliage application, soil application, or water surface application, for the purpose of controlling various agricultural pests, mites and nematodes.

Specific examples of the various agricultural pests, mites and nematodes that can be controlled by the pest control agent of the present invention are listed below.

(1) Lepidoptera Butterflies and Moths (a) Arctiidae moths, for example, *Hyphantria cunea* and *Lemyra imparilis*;

(b) Bucculatricidae moths, for example, *Bucculatrix pyrivorella*;

(c) Carposinidae, for example, *Carposina sasakii*;

(d) Crambidae moths, for example, *Diaphania indica* and *Diaphania nitidalis* of *Diaphania* spp.; *Ostrinia furnacalis*, *Ostrinia nubilalis* and *Ostrinia scapulalis* of *Ostrinia* spp.; and others such as *Chilo suppressalis, Cnaphalocrocis medinalis, Conogethes punctiferalis, Diatraea grandiosella, Glyphodes pyloalis, Hellula undalis* and *Parapediasia teterrella*;

(e) Gelechiidae moths, for example, *Helcystogramma triannulella, Pectinophora gossypiella, Phthorimaea operculella* and *Sitotroga cerealella*;

(f) Geometridae moths, for example, *Ascotis selenaria*;

(g) Gracillariidae moths, for example, *Caloptilia theivora, Phyllocnistis citrella* and *Phyllonorycter ringoniella*;

(h) Hesperiidae butterflies, for example, *Parnara guttata*;

(i) Lasiocampidae moths, for example, *Malacosoma neustria*;

(j) Lymantriidae moths, for example, *Lymantria dispar* and *Lymantria monacha* of *Lymantria* spp.; and others such as *Euproctis pseudoconspersa* and *Orgyia thyellina*;

(k) Lyonetiidae moths, for example, *Lyonetia clerkella* and *Lyonetia prunifoliella malinella* of *Lyonetia* spp.;

(l) Noctuidae moths, for example, *Spodoptera depravata, Spodoptera eridania, Spodoptera exigua, Spodoptera frugiperda, Spodoptera littoralis* and *Spodoptera litura* of *Spodoptera* spp.; *Autographa gamma* and *Autographa nigrisigna* of *Autographa* spp.; *Agrotis ipsilon* and *Agrotis segetum* of *Agrotis* spp.; *Helicoverpa armigera, Helicoverpa assulta* and *Helicoverpa zea* of *Helicoverpa* spp.; *Heliothis armigera* and *Heliothis virescens* of *Heliothis* spp.; and others such as *Aedia leucomelas, Ctenoplusia agnata, Eudocima tyrannus, Mamestra brassicae, Mythimna separata, Naranga aenescens, Panolis japonica, Peridroma saucia, Pseudoplusia includens* and *Trichoplusia ni*;

(m) Nolidae moths, for example, *Earias insulana*;

(n) Pieridae butterflies, for example, *Pieris brassicae* and *Pieris rapae crucivora* of *Pieris* spp.;

(o) Plutellidae moths, for example, *Acrolepiopsis sapporensis* and *Acrolepiopsis suzukiella* of *Acrolepiopsis* spp.; and others such as *Plutella xylostella*;

(p) Pyralidae moths, for example, *Cadra cautella, Elasmopalpus lignosellus, Etiella zinckenella* and *Galleria mellonella*;

(q) Sphingidae moths, for example, *Manduca quinquemaculata* and *Manduca sexta* of *Manduca* spp.;

(r) Stathmopodidae moths, for example, *Stathmopoda masinissa*;

(s) Tineidae moths, for example, *Tinea translucens*;

(t) Tortricidae moths, for example, *Adoxophyes honmai* and *Adoxophyes orana* of *Adoxophyes* spp.; *Archips breviplicanus* and *Archips fuscocupreanus* of *Archips* spp.; and others such as *Choristoneura fumiferana, Cydia pomonella, Eupoecilia ambiguella, Grapholitha molesta, Homona magnanima, Leguminivora glycinivorella, Lobesia botrana, Matsumuraeses phaseoli, Pandernis heparana* and *Sparganothis pilleriana*; and (u) Yponomeutidae moths, for example, *Argyresthia conjugella*.

(2) Thysanoptera Insect Pests (a) Phlaeothripidae, for example, *Ponticulothrips diospyrosi*; and (b) Thripidae, for example, *Frankliniella intonsa* and *Frankliniella occidentalis* of *Frankliniella* spp.; *Thrips palmi* and *Thrips tabaci* of *Thrips* spp.; and others such as *Heliothrips haemorrhoidalis* and *Scirtothrips dorsalis*.

(3) Hemiptera Insect Pests (A) Archaeorrhyncha (a) Delphacidae, for example, *Laodelphax striatella, Nilaparvata lugens, Perkinsiella saccharicida* and *Sogatella furcifera*.

(B) Clypeorrhyncha (a) Cicadellidae, for example, *Empoasca fabae, Empoasca nipponica, Empoasca onukii* and *Empoasca sakaii* of *Empoasca* spp.; and others such as *Arboridia apicalis, Balclutha saltuella, Epiacanthus stramineus, Macrosteles striifrons* and *Nephotettix cincticeps*.

(C) Heteroptera (a) Alydidae, for example, *Riptortus clavatus*;

(b) Coreidae, for example, *Cletus punctiger* and *Leptocorisa chinensis*;

(c) Lygaeidae, for example, *Blissus leucopterus, Cavelerius saccharivorus* and *Togo hemipterus*;

(d) Miridae, for example, *Halticus insularis, Lygus lineolaris, Psuedatomoscelis seriatus, Stenodema sibiricum, Stenotus rubrovittatus* and *Trigonotylus caelestialium*;

(e) Pentatomidae, for example, *Nezara antennata* and *Nezara viridula* of *Nezara* spp.; *Eysarcoris aeneus, Eysarcoris lewisi* and *Eysarcoris ventralis* of *Eysarcoris* spp.; and others such as *Dolycoris baccarum, Eurydema rugosum, Glaucias subpunctatus, Halyomorpha halys, Piezodorus hybneri, Plautia crossota* and *Scotinophora lurida*;

(f) Pyrrhocoridae, for example, *Dysdercus cingulatus*;

(g) Rhopalidae, for example, *Rhopalus msculatus*;

(h) Scutelleridae, for example, *Eurygaster integriceps*; and (i) Tingidae, for example, *Stephanitis nashi*.

(D) Sternorrhyncha (a) Adelgidae, for example, *Adelges laricis*;

(b) Aleyrodidae, for example, *Bemisia argentifolii* and *Bemisia tabaci* of *Bemisia* spp.; and others such as *Aleurocanthus spiniferus, Dialeurodes citri* and *Trialeurodes vaporariorum*;

(c) Aphididae, for example, *Aphis craccivora, Aphis fabae, Aphis forbesi, Aphis gossypii, Aphis pomi, Aphis sambuci* and *Aphis spiraecola* of *Aphis* spp.; *Rhopalosiphum maidis* and *Rhopalosiphum padi* of *Rhopalosiphum* spp.; *Dysaphis plantaginea* and *Dysaphis radicola* of *Dysaphis* spp.; *Macrosiphum avenae* and *Macrosiphum euphorbiae* of *Macrosiphum* spp.; *Myzus cerasi, Myzus persicae* and *Myzus varians* of *Myzus* spp.; and others such as *Acyrthosiphon pisum, Aulacorthum solani, Brachycaudus helichrysi, Brevicoryne brassicae, Chaetosiphon fragaefolii, Hyalopterus pruni, Hyperomyzus lactucae, Lipaphis erysimi, Megoura viciae, Metopolophium dirhodum, Nasonovia ribis-nigri, Phorodon humuli, Schizaphis graminum, Sitobion avenae* and *Toxoptera aurantii*;

(d) Coccidae, for example, *Ceroplastes ceriferus* and *Ceroplastes rubens* of *Ceroplastes* spp.;

(e) Diaspididae, for example, *Pseudaulacaspis pentagona* and *Pseudaulacaspis prunicola* of *Pseudaulacaspis* spp.; *Unaspis euonymi* and *Unaspis yanonensis* of *Unaspis* spp.; and others such as *Aonidiella aurantii, Comstockaspis perniciosa, Fiorinia theae* and *Pseudaonidia paeoniae*;

(f) Margarodidae, for example, *Drosicha corpulenta* and *Icerya purchasi*;

(g) Phylloxeridae, for example, *Viteus vitifolii*;

(h) Pseudococcidae, for example, *Planococcus citri* and *Planococcus kuraunhiae* of *Planococcus* spp.; and others such as *Phenacoccus solani* and *Pseudococcus comstocki*; and (i) Psyllidae, for example, *Psylla mali* and *Psylla pyrisuga* of *Psylla* spp.; and others such as *Diaphorina citri*.

(4) Polyphaga Insect Pests (a) Anobiidae, for example, *Lasioderma serricorne*;

(b) Attelabidae, for example, *Byctiscus betulae* and *Rhynchites heros*;

(c) Bostrichidae, for example, *Lyctus brunneus*;

(d) Brentidae, for example, *Cylas formicarius*;

(e) Buprestidae, for example, *Agrilus sinuatus*;

(f) Cerambycidae, for example, *Anoplophora malasiaca*, *Monochamus alternatus*, *Psacothea hilaris* and *Xylotrechus pyrrhoderus*;

(g) Chrysomelidae, for example, *Bruchus pisorum* and *Bruchus rufimanus* of *Bruchus* spp.; *Diabrotica barberi*, *Diabrotica undecimpunctata* and *Diabrotica virgifera* of *Diabrotica* spp.; *Phyllotreta nemorum* and *Phyllotreta striolata* of *Phyllotreta* spp.; and others such as *Aulacophora femoralis*, *Callosobruchus chinensis*, *Cassida nebulosa*, *Chaetocnema concinna*, *Leptinotarsa decemlineata*, *Oulema oryzae* and *Psylliodes angusticollis*;

(h) Coccinellidae, for example, *Epilachna varivestis* and *Epilachna vigintioctopunctata* of *Epilachna* spp.;

(i) Curculionidae, for example, *Anthonomus grandis* and *Anthonomus pomorum* of *Anthonomus* spp.; *Sitophilus granarius* of *Sitophilus zeamais* of *Sitophilus* spp.; and others such as *Echinocnemus squameus*, *Euscepes postfasciatus*, *Hylobius abietis*, *Hypera postica*, *Lissohoptrus oryzophilus*, *Otiorhynchus sulcatus*, *Sitona lineatus* and *Sphenophorus venatus*;

(j) Elateridae, for example, Melanotus fortnumni and Melanotus tamsuyensis of Melanotus spp.;

(k) Nitidulidae, for example, *Epuraea domina*;

(L) Scarabaeidae, for example, *Anomala cuprea* and *Anomala rufocuprea* of *Anomala* spp.; and others such as *Cetonia aurata*, *Gametis jucunda*, *Heptophylla picea*, *Melolontha melolontha* and *Popillia japonica*;

(m) Scolytidae, for example, *Ips typographus*;

(n) Staphylinidae, for example, *Paederus fuscipes*;

(o) Tenebrionidae, for example, *Tenebrio molitor* and *Tribolium castaneum*; and (p) Trogossitidae, for example, *Tenebroides mauritanicus*.

(5) Diptera Insect Pests (A) Brachycera (a) Agromyzidae, for example, *Liriomyza bryoniae*, *Liriomyza chinensis*, *Liriomyza sativae* and *Liriomyza trifolii* of *Liriomyza* spp.; and others such as *Chromatomyia horticola* and *Agromyza oryzae*;

(b) Anthomyiidae, for example, *Delia platura* and *Delia radicum* of *Delia* spp.; and others such as *Pegomya cunicularia*;

(c) Drosophilidae, for example, *Drosophila melanogaster* and *Drosophila suzukii* of *Drosophila* spp.;

(d) Ephydridae, for example, *Hydrellia griseola*;

(e) Psilidae, for example, *Psila rosae*; and (f) Tephritidae, for example, *Bactrocera cucurbitae* and *Bactrocera dorsalis* of *Bactrocera* spp.; *Rhagoletis cerasi* and *Rhagoletis pomonella* of *Rhagoletis* spp.; and others such as *Ceratitis capitata* and *Dacus oleae*.

(B) Nematocera (a) Cecidomyiidae, for example, *Asphondylia yushimai*, *Contarinia sorghicola*, *Mayetiola destructor* and *Sitodiplosis mosellana*.

(6) Orthoptera Insect Pests (a) Acrididae, for example, *Schistocerca americana* and *Schistocerca gregaria* of *Schistocerca* spp.; and others such as *Chortoicetes terminifera*, *Dociostaurus maroccanus*, *Locusta migratoria*, *Locustana pardalina*, *Nomadacris septemfasciata* and *Oxya yezoensis*;

(b) Gryllidae, for example, *Acheta domestica* and *Teleogryllus emma*;

(c) Gryllotalpidae, for example, *Gryllotalpa orientalis*; and (d) Tettigoniidae, for example, *Tachycines asynamorus*.

(7) Acari (A) Acaridida of Astigmata (a) Acaridae mites, for example, *Rhizoglyphus echinopus* and *Rhizoglyphus robini* of *Rhizoglyphus* spp.; *Tyrophagus neiswanderi*, *Tyrophagus perniciosus*, *Tyrophagus putrescentiae* and *Tyrophagus similis* of *Tyrophagus* spp.; and others such as *Acarus siro*, *Aleuroglyphus ovatus* and *Mycetoglyphus fungivorus*;

(B) Actinedida of Prostigmata (a) Tetranychidae mites, for example, *Bryobia praetiosa* and *Bryobia rubrioculus* of *Bryobia* spp.; *Eotetranychus asiaticus*, *Eotetranychus boreus*, *Eotetranychus celtis*, *Eotetranychus geniculatus*, *Eotetranychus kankitus*, *Eotetranychus pruni*, *Eotetranychus shii*, *Eotetranychus smithi*, *Eotetranychus suginamensis* and *Eotetranychus uncatus* of *Eotetranychus* spp.; *Oligonychus hondoensis*, *Oligonychus ilicis*, *Oligonychus karamatus*, *Oligonychus mangiferus*, *Oligonychus orthius*, *Oligonychus perseae*, *Oligonychus pustulosus*, *Oligonychus shinkajii* and *Oligonychus ununguis* of *Oligonychus* spp.; *Panonychus citri*, *Panonychus mori* and *Panonychus ulmi* of *Panonychus* spp.; *Tetranychus cinnabarinus*, *Tetranychus kanzawai*, *Tetranychus ludeni*, *Tetranychus quercivorus*, *Tetranychus phaselus*, *Tetranychus urticae* and *Tetranychus viennensis* of *Tetranychus* spp.; *Aponychus corpuzae* and *Aponychus firmianae* of *Aponychus* spp.; *Sasanychus akitanus* and *Sasanychus pusillus* of *Sasanychus* spp.; *Shizotetranychus celarius*, *Shizotetranychus longus*, *Shizotetranychus miscanthi*, *Shizotetranychus recki* and *Shizotetranychus schizopus* of *Shizotetranychus* spp.; and others such as *Tetranychina harti*, *Tuckerella pavoniformis* and *Yezonychus sapporensis*;

(b) Tenuipalpidae mites, for example, *Brevipalpus lewisi*, *Brevipalpus obovatus*, *Brevipalpus phoenicis*, *Brevipalpus russulus* and *Brevipalpus californicus* of *Brevipalpus* spp.; *Tenuipalpus pacificus* and *Tenuipalpus zhizhilashviliae* of *Tenuipalpus* spp.; and others such as *Dolichotetranychus floridanus*;

(c) Eriophyidae mites, for example, *Aceria diospyri*, *Aceria ficus*, *Aceria japonica*, *Aceria kuko*, *Aceria paradianthi*, *Aceria tiyingi*, *Aceria tulipae* and *Aceria zoysiea* of *Aceria* spp.; *Eriophyes chibaensis* and *Eriophyes emarginatae* of *Eriophyes* spp.; *Aculops lycopersici* and *Aculops pelekassi* of *Aculops* spp.; *Aculus fockeui* and *Aculus schlechtendali* of *Aculus* spp.; and others such as *Acaphylla theavagrans*, *Calacarus carinatus*, *Colomerus vitis*, *Calepitrimerus vitis*, *Epitrimerus pyri*, *Paraphytoptus kikus*, *Paracalacarus podocarpi* and *Phyllocotruta citri*;

(d) Transonemidae mites, for example, *Tarsonemus bilobatus* and *Tarsonemus waitei* of *Tarsonemus* spp.; and others such as *Phytonemus pallidus* and *Polyphagotarsonemus latus*; and (e) Penthaleidae mites, for example, *Penthaleus erythrocephalus* and *Penthaleus major* of *Penthaleus* spp.

(8) Phytoparasitic Nematodes (A) Tylenchida (a) Anguinidae, for example, *Anguina funesta* and *Anguina tritici* of *Anguina* spp.; and *Ditylenchus destructor*, *Ditylenchus dipsaci* and *Ditylenchus myceliophagus* of *Ditylenchus* spp.;

(b) Aphelenchoididae, for example, *Aphelenchoides besseyi*, *Aphelenchoides fragariae*, *Aphelenchoides ritzemabosi* and *Aphelenchoides besseyi* of *Aphelenchoides* spp.; and *Bursaphelenchus xylophilus* of *Bursaphelenchus* spp.;

(c) Belonolaimidae, for example, *Belonolaimus longicaudatus* of *Belonolaimus* spp.; and *Tylenchorhynchus claytoni* and *Tylenchorhynchus dubius* of *Tylenchorhynchus* spp.;

(d) Criconematidae, for example, *Criconema mutabile;*

(e) Dolichodoridae, for example, *Dolichodorus mediterraneus;*

(f) Ecphyadophoridae, for example, *Ecphyadophora tenuissima;*

(g) Hemicycliophoridae, for example, *Loofia thienemanni*

(h) Heteroderidae, for example, *Globodera rostochiensis*, *Globodera pallida* and *Globodera tabacum* of *Globodera* spp.; and *Heterodera avenae*, *Heterodera cruciferae*, *Heterodera glycines*, *Heterodera schachtii* and *Heterodera trifolii* of *Heterodera* spp.;

(i) Hoplolaimidae, for example, *Helicotylenchus dihystera* and *Helicotylenchus multicinctus* of *Helicotylenchus* spp.; *Hoplolaimus columbus* and *Hoplolaimus galeatus* of *Hoplolaimus* spp.; and others such as *Rotylenchus robustus* and *Rotylenchulus reniformis;*

(j) Meloidogynidae, for example, *Meloidogyne arenaria*, *Meloidogyne chitwoodi*, *Meloidogyne hapla*, *Meloidogyne incognita*, *Meloidogyne javanica* and *Meloidogyne thamesi* of *Meloidogyne* spp.;

(k) Nothotylenchidae, for example, *Nothotylenchus acris;*

(l) Paratylenchidae, for example, *Paratylenchus curvitatus* and *Paratylenchus elachistus* of *Paratylenchus* spp.; and (m) Pratylenchidae, for example, *Pratylenchus brachyurus*, *Pratylenchus coffeae*, *Pratylenchus curvitatus*, *Pratylenchus fallax*, *Pratylenchus goodeyi*, *Pratylencus neglectus*, *Pratylenchus penetrans*, *Pratylenchus scribneri*, *Pratylenchus vulnus* and *Pratylenchus zeae* of *Pratylenchus* spp.; and others such as *Nacobbus aberrans*, *Radopholus similis*, *Tylenchulus semnipenetrans* and *Radopholus citrophilus*.

(B) Dorylaimida (a) Longidoridae, for example, *Longidorus elongates* of *Longidorus* spp.; and *Xiphinema americanum*, *Xiphinema brevicolle*, *Xiphinema index* and *Xiphinema diversicaudatum* of *Xiphinema* spp.

(C) Triplonchida (a) Trichodoridae, for example, *Trichodorus primitivus* and *Paratrichodorus minor.*

The pest control agent of the present invention may be mixed or used in combination with other active constituents such as fungicides, insecticides and miticides, nematicides and soil pesticides; and/or plant regulators, herbicides, synergists, fertilizers, soil conditioners and animal feed.

Combinations of the compound of the present invention with other active constituents can be expected to provide synergistic effects in terms of insecticide, miticide and nematicide activity. This type of synergistic effect can be confirmed using the Colby equation in accordance with typical methods (Colby, S. R.; Calculating Synergistic and Antagonistic Responses of Herbicide Combinations; Weeds 15, pp. 20 to 22, 1967).

Specific examples of insecticides, miticides, nematicides, soil pesticides, and parasiticides and the like that can be mixed or used in combination with the pest control agent of the present invention are listed below.

(1) Acetylcholinesterase inhibitors:

(a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylycarb; fenothiocarb, MIPC, MPMC, MTMC, aldoxycarb, allyxycarb, aminocarb, bufencarb, cloethocarb, metam-sodium, and promecarb; and (2) Organophosphorus-based: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinfos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridafenthion, quinalphos, sulfotep, tebupirimfos, temephos, terbufos, tetrachlorvinphos, thiometon, triazophos, trichlorfon, vamidothion; bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazophos, iodofenphos, methacrifos, pirimiphos-ethyl, phosphocarb, propaphos, prothoate, and sulprofos.

(2) GABA receptor chloride ion channel antagonists: acetoprole, chlordane, endosulfan, ethiprole, fipronil, pyrafluprole, pyriprole; camphechlor, heptachlor, and dienochlor.

(3) Sodium channel modulators: acrinathrin, d-cis/trans-allethrin, d-trans-allethrin, bifenthrin, bioallethrin, bioallethrin S-cyclopentyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], delta-methrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin [(1R)-isomer], tralomethrin, transfluthrin; allethrin, pyrethrin, pyrethrin I, pyrethrin II, profluthrin, dimefluthrin, bioethanomethrin, biopermethrin, transpermethirn, fenfluthrin, fenpyrithrin, flubrocythrinate, flufenoprox, metofluthrin, protrifenbute, pyresmethrin, and terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, and flupyradifurone.

(5) Nicotinic acetylcholine receptor allosteric modulators: spinetoram and spinosad.

(6) Chloride channel activators: abamectin, emamectin-benzoate, lepimectin, milbemectin; ivermectin, seramectin, doramectin, eprinomectin, moxidectin; milbemycin, milbemycin oxime, and nemadectin.

(7) Juvenile hormone-like substances: hydroprene, kinoprene, methoprene, fenoxycarb, pyriproxyfen; diofenolan, epofenonane, and triprene.

(8) Other nonspecific inhibitors: methyl bromide, chloropicrin, sulfuryl fluoride, borax, and tartar emetic.

(9) Homoptera selective feeding inhibitors: flonicamid, pymetrozine, and pyrifluquinazon.
(10) Mite growth inhibitors: clofentezine, diflovidazin, hexythiazox, and etoxazole.
(11) Microorganism-derived insect midgut inner membrane disrupting agents: *Bacillus thuringiensis* subsp. *israelensis*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, Bt crop protein: Cry1Ab, Cry1Ac, Cry1Fa, Cry1A.105, Cry2Ab, Vip3A, mCry3A, Cry3Ab, Cry3Bb, Cry34Abl/Cry35Abl.
(12) Mitochondria ATP biosynthesis enzyme inhibitors: diafenthiuron, azocyclotin, cyhexatin, fenbutatin oxide, propargite, and tetradifon.
(13) Oxidative phosphorylation uncoupling agents: chlorfenapyr, sulfluramid, DNOC; binapacryl, dinobuton, and dinocap.
(14) Nicotinic acetylcholine receptor channel blockers: bensultap, cartap hydrochloride; nereistoxin; thiosultap-sodium, and thiocyclarm.
(15) Chitin synthesis inhibitors: bistrifluron, chlorfluazuron, diflubenzuron, flucycloxuron, flufenoxuron, hexaflumuron, lufenuron, novaluron, novifumuron, teflubenzuron, triflumuron, buprofezin, and fluazuron.
(16) Diptera molting disturbing agent: cyromazine.
(17) Molting hormone receptor agonists: chromafenozide, halofenozide, methoxyfenozide, and tebufenozide.
(18) Octopamine receptor agonists: amitraz, demiditraz, and chlordimeform
(19) Mitochondria electron transfer chain complex III inhibitors: acequinocyl, fluacrypyrim, and hydramethylnon.
(20) Mitochondria electron transfer chain complex I inhibitors: fenazaquin, fenproximate, pyrimidifen, pyridaben, tebufenpyrad, tolfenpyrad, and rotenone.
(21) Voltage-dependent sodium channel blockers: indoxacarb and metaflumizone.
(22) Acetyl CoA carboxylase inhibitors: spirodiclofen, spiromesifen, and spirotetramat.
(23) Mitochondria electron transfer chain complex IV inhibitors: aluminium phosphide, calcium phosphide, phosphine, zinc phosphide, and cyanide.
(24) Mitochondria electron transfer chain complex II inhibitors: cyenopyrafen, cyflumetofen, and pyflubumide.
(25) Ryanodine receptor modulators: chlorantraniliprole, cyantraniliprole, flubendiamide, cyclaniliprole, and tetraniliprole.
(26) Mixed function oxidase inhibitor compound: piperonyl butoxide.
(27) Latrophilin receptor agonists: depsipeptide, cyclodepsipeptide, 24-membered cyclodepsipeptide, emodepside.
(28) Others (for which the mode of action is unknown): azadirachtin, benzoximate, bifenazate, bromopropylate, quinomethionate, cryolite, dicofol, pyridalyl; benclothiaz, sulfur, amidoflumet, 1,3-dichloropropene, DCIP, phenisobromolate, benzomate, metaldehyde, chlorobenzilate, chlothiazoben, dicyclanil, fenoxacrim, fentrifanil, flubenzimine, fluphenazine, gossyplure, japonilure, metoxadiazone, oil, potassium oleate, tetrasul, triarathene; afidopyropen, flometoquin, flufiprole, fluensulfone, meperfluthrin, tetramethylfluthrin, tralopyril, dimefluthrin, methylneodecanamide; fluralaner, afoxolaner, fluxametamide,5-[5-(3,5-dichlorophenyl)-5-trifluoromethyl-4,5-dihydroisoxazol-3-yl]-2-(1H-1,2,4-triazol-1-yl)benzonitrile (CAS:943137-49-3), broflanilide, and other meta-diamides.
(29) Parasiticides:
(a) Benzimidazole-based: fenbendazole, albendazole, triclabendazole, oxibendazole, mebendazole, oxfendazole, parbendazole, flubendazole; febantel, netobimin, thiophanate; thiabendazole, and cambendazole;
(b) Salicylanilide-based: closantel, oxyclozanide, rafoxanide, and niclosamide;
(c) Substituted phenol-based: nitroxinil, nitroscanate;
(d) Pyrimidine-based: pyrantel and morantel;
(e) Imidazothiazole-based: levamisole and tetramisole;
(f) Tetrahydropyrimidine-based: praziquantel and epsiprantel; and
(g) Other parasiticides: cyclodiene, ryania, clorsulon, metronidazole, demiditraz; piperazine, diethylcarbamazine, dichlorophen, monepantel, tribendimidine, amidantel; thiacetarsamide, melarsomine, and arsenamide.

Specific examples of fungicides that can be mixed or used in combination with the pest control agent of the present invention are listed below.
(1) Nucleic acid biosynthesis inhibitors:
(a) RNA polymerase I inhibitors: benalaxyl, benalaxyl-M, furalaxyl, metalaxyl, metalaxyl-M, oxadixyl; clozylacon, and ofurace;
(b) Adenosine deaminase inhibitors: bupirimate, dimethirimol, and ethirimol;
(c) DNA/RNA synthesis inhibitors: hymexazol and octhilinone; and
(d) DNA topoisomerase II inhibitor: oxolinic acid.
(2) Mitotic inhibitors and cell division inhibitors:
(a) β-tubulin polymerization inhibitors: benomyl, carbendazim, chlorfenazole, fuberidazole, thiabendazole; thiophanate, thiophanate-methyl; diethofencarb; zoxamide; and ethaboxam;
(b) Cell division inhibitor: pencycuron; and
(c) Delocalization inhibitor of spectrin-like proteins: fluopicolide.
(3) Respiration inhibitors:
(a) Complex I NADH oxidoreductase inhibitors: diflumetorim and tolfenpyrad;
(b) Complex II succinic acid dehydrogenase inhibitors: benodanil, flutolanil, mepronil; isofetamid, fluopyram; fenfuram, furmecyclox; carboxin, oxycarboxin; thifluzamide; benzovindiflupyr, bixafen, fluxapyroxad, furametpyr, isopyrazam, penflufen, penthiopyrad, sedaxane; and boscalid;
(c) Complex III ubiquinol oxidase Qo inhibitors: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoximmethyl, trifloxystrobin; dimoxystrobin, fenaminstrobin, metominostrobin, orysastrobin; famoxadone; fluoxastrobin; fenamidone; and pyribencarb;
(d) Complex III ubiquinol reductase Qi inhibitors: cyazofamid and amisulbrom;
(e) Oxidative phosphorylation uncoupling agents: binapacryl, meptyldinocap, dinocap; fluazinam; and ferimzone;
(f) Oxidative phosphorylation inhibitors (ATP synthase inhibitors): fentin acetate, fentin chloride, and fentin hydroxide;
(g) ATP production inhibitor: silthiofam; and
(h) Complex III cytochrome bc1 (ubiquinone reductase) Qx (unknown) inhibitor: ametoctradin;
(4) Amino acid and protein synthesis inhibitors
(a) Methionine biosynthesis inhibitors: andoprim, cyprodinil, mepanipyrim, and pyrimethanil; and
(b) Protein synthesis inhibitors: blasticidin-S; kasugamycin; kasugamycin hydrochloride; streptomycin; and oxytetracycline.
(5) Signal transduction inhibitors:
(a) Signal transduction inhibitors: quinoxyfen and proquinazid; and (b) MAP/histidine kinase inhibitors in osmotic pressure signal transduction: fenpiclonil, fludioxonil; chlozolinate, iprodione, procymidone, and vinclozolin.
(6) Lipid and cell membrane synthesis inhibitors:
(a) Phospholipid biosynthesis and methyltransferase inhibitors: edifenphos, iprobenfos, pyrazophos; and isoprothiolane;
(b) Lipid peroxidation agents: biphenyl, chloroneb, dichloran, quintozene, tecnazene, tolclofos-methyl; and etridiazole;
(c) Agents that act upon cell membranes: iodocarb, propamocarb, propamocarb-hydrochloride, propamocarb-fosetylate, and prothiocarb;
(d) Microorganisms that disturb pathogen cell membranes: *Bacillus subtilis, Bacillus subtilis* strain QST713, *Bacillus subtilis* strain FZB24, *Bacillus subtilis* strain MBI600, and *Bacillus subtilis* strain D747; and
(e) Agents that disturb cell membranes: *Melaleuca alternifolia* (tea tree) extract.
(7) Cell membrane sterol biosynthesis inhibitors:
(a) C14 position demethylation inhibitors in sterol biosynthesis: triforine; pyrifenox, pyrisoxazole; fenarimol, flurprimidol, nuarimol; imazalil, imazalil-sulfate, oxpoconazole, pefurazoate, prochloraz, triflumizole, viniconazole; azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, quinconazole, simeconazole, tebuconazole, tetraconazole, triadimefon, triadimenol, triticonazole; prothioconazole, and voriconazole;
(b) Δ14 reductase and Δ8→Δ7-isomerase inhibitors in sterol biosynthesis: aldimorph, dodemorph, dodemorph acetate, fenpropimorph, tridemorph; fenpropidin, piperalin; and spiroxamine;
(c) 3-keto reductase inhibitors in C4-position demethylation in sterol biosynthesis systems: fenhexamid and fenpyrazamine; and
(d) Squalene epoxidase inhibitors in sterol biosynthesis systems: pyributicarb; naftifene, and terbinafine.
(8) Cell wall synthesis inhibitors:
(a) Trehalase inhibitor: validamycin;
(b) Chitin synthase inhibitors: polyoxins and polyoxorim; and
(c) Cellulose synthase inhibitors: dimethomorph, flumorph, pyrimorph; benthiavalicarb, iprovalicarb, tolprocarb, valifenalate; and mandipropamide.
(9) Melanin biosynthesis inhibitors:
(a) Reductase inhibitors in melanin biosynthesis: fthalide; pyroquilon; and tricyclazole; and
(b) Anhydrase inhibitors in melanin biosynthesis: carpropamid; diclocymet; and fenoxanil.
(10) Host plant resistance-inducing agents:
(a) Agent that acts on salicylic acid biosynthetic pathway: acibenzolar-S-methyl; and
(b) Others: probenazole; tiadinil; isotianil; laminarin; and *Reynoutria sachalinensis* extract.
(11) Agents for which the mode of activity is unclear: cymoxanil, fosetyl-aluminum, phosphoric acid (phosphate), tecloftalam, triazoxide, flusulfamide, diclomezine, methasulfocarb, cyflufenamid, metrafenone, pyriofenone, dodine, dodine free base, and flutianil.
(12) Agents having multiple activities: copper (copper salts), bordeaux mixture, copper hydroxide, copper naphthalate, copper oxide, copper oxychloride, copper sulfate, sulfur, sulfur products, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine triacetate, iminoctadine trialbesilate; anilazine; dithianon; quinomethionate; and fluoroimide.
(13) Other agents: DBEDC, fluorofolpet, guazatine acetate, bis(8-quinolinolato) copper(II), propamidine, chloropicrin, cyprofuram, agrobacterium, bethoxazin, diphenylamine, methyl isothiocyanate (MITC), mildiomycin, capsaicin, curfraneb, cyprosulfamide, dazomet, debacarb, dichlorophen, difenzoquat, difenzoquat methyl sulfonate, flumetover, fosetyl-calcium, fosetyl-sodium, irumamycin, natamycin, nitrothal-isopropyl, oxamocarb, puropamocin sodium, pyrrolnitrin, tebufloquin, tolnifanide, zarilamide, Algophase, Amicarthiazol, Oxathiapiprolin, metiram-zinc, benthiazole, trichlamide, uniconazole, mildiomycin, Oxyfenthiin, and picarbutrazox.

Specific examples of plant growth regulators that can be mixed or used in combination with the pest control agent of the present invention are listed below.

Abscisic acid, kinetin, benzylaminopurine, 1,3-diphenylurea, forchlorfenuron, thidiazuron, chlorfenuron, dihydrozeatin, gibberellin A, gibberellin A4, gibberellin A7, gibberellin A3, 1-methylcyclopropane, N-acetyl aminoethoxyvinylglycine (alternative name: aviglycine), aminooxyacetate, silver nitrate, cobalt chloride, IAA, 4-CPA, cloprop, 2,4-D, MCPB, indole-3-butyric acid, dichlorprop, phenothiol, 1-naphthylacetamide, ethychlozate, cloxyfonac, maleic acid hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl)aminobutyric acid; ethephon, chlormequat, mepiquat chloride, benzyl adenine, and 5-aminolevulinic acid.

[Endoparasite Control Agent or Parasiticide]

An endoparasite control agent or parasiticide of the present invention contains at least one compound selected from the sufonylaminobenzamide compounds of the present invention as an active constituent.

The parasites targeted by the endoparasite control agent or parasiticide of the present invention live inside the bodies of host animals, and particularly inside the bodies of warm-blooded animals and fish (namely, endoparasites). Examples of host animals for which the endoparasite control agent or parasiticide of the present invention is effective include warm-blooded animals such as humans, domestic mammals (for example, cows, horses, pigs, sheep, and goats and the like), experimental animals (for example, mice, rats, and gerbils and the like), pet animals (for example, hamsters, guinea pigs, dogs, cats, horses, squirrels, rabbits, and ferrets and the like), wild mammals and zoo mammals (for example, monkeys, foxes, deer, and buffalo and the like), domestic fowl (for example, turkeys, ducks, chickens, and quail and the like), pet birds (for example, pigeons, parrots, myna birds, Java finches, parakeets, Bengalese finches, and canaries and the like); and fishes such as salmon, trout, and koi carp and the like. By controlling or exterminating the parasites, parasitic diseases carried by the parasites can be prevented or treated.

Examples of parasites that can be controlled or exterminated include those listed below.

(1) Dioctophymatida nematodes
(a) Kidney worms of the Dioctophymatidae family, for example, *Dioctophyma renale* of *Dioctophyma* spp.; and
(b) Kidney worms of the Soboliphymlatidae family, for example, *Soboliphyme abei* and *Soboliphyme baturini* of *Soboliphyme* spp.

(2) Trichocephalida nematodes
(a) Trichina worms of the Trichinellidae family, for example, *Trichinella spiralis* of *Trichinella* spp.; and
(b) Whipworms of the Trichuridae family, for example, *Capillaria annulata, Capillaria contorta, Capillaria hepatica, Capillaria perforans, Capillaria plica* and *Capillaria suis* of *Capillaria* spp.; and *Trichuris vulpis, Trichuris discolor, Trichuris ovis, Trichuris skrjabini* and *Trichuris suis* of *Trichuris* spp.
(3) Rhabditida nematodes
Threadworms of the Strongyloididae family, for example, *Strongyloides papillosus, Strongyloides planiceps, Strongyloides ransomi, Strongyloides suis, Strongyloides stercoralis, Strongyloides tumefaciens* and *Strongyloides ratti* of *Strongyloides* spp.
(4) Strongylida nematodes
Hookworms of the Ancylostomatidae family, for example, *Ancylostoma braziliense, Ancylostoma caninum, Ancylostoma duodenale* and *Ancylostoma tubaeforme* of *Ancylostoma* spp.; *Uncinaria stenocephala* of *Uncinaria* spp.; and *Bunostomum phlebotounm* and *Bunostomum trigonocephalum* of *Bunostomum* spp.
(5) Strongylida nematodes
(a) Nematodes of the Angiostrongylidae family, for example, *Aelurostrongylus abstrusus* of *Aelurostrongylus* spp.; and *Angiostrongylus vasorum* and *Angiostrongylus cantonesis* of *Angiostrongylus* spp.;
(b) Nematodes of the Crenosomatidae family, for example, *Crenosoma aerophila* and *Crenosoma vulpis* of *Crenosoma* spp.;
(c) Nematodes of the Filaroididae family, for example, *Filaroides hirthi* and *Filaroides osleri* of *Filaroides* spp.;
(d) Lungworms of the Metastrongylidae family, for example, *Metastrongylus apri, Metastrongylus asymmetricus, Metastrongylus pudendotectus* and *Metastrongylus salmi* of *Metastrongylus* spp.; and
(e) Gapeworms of the Syngamidae family, for example, *Cyathostoma bronchialis* of *Cyathostoma* spp.; and *Syngamus skrjabinomorpha* and *Syngamus trachea* of *Syngamus* spp.
(6) Strongylida nematodes
(a) Nematodes of the Molineidae family, for example, *Nematodirus filicollis* and *Nematodirus spathiger* of *Nematodirus* spp.;
(b) Nematodes of the Dictyocaulidae family, for example, *Dictyocaulus filarial* and *Dictyocaulus viviparus* of *Dictyocaulus* spp.;
(c) Nematodes of the Haemonchidae family, for example, *Haemonchus contortus* of *Haemonchus* spp.; and *Mecistocirrus digitatus* of *Mecistocirrus* spp.; (d) Nematodes of the Haemonchidae family, for example, *Ostertagia ostertagi* of *Ostertagia* spp.;
(e) Nematodes of the Heligmonellidae family, for example, *Nippostrongylus braziliensis* of *Nippostrongylus* spp.; and
(f) Nematodes of the Trichostrongylidae family, for example, *Trichostrongylus axei, Trichostrongylus colubriformis* and *Trichostrongylus tenuis* of *Trichostrongylus* spp.; *Hyostrongylus rubidus* of *Hyostrongylus* spp.; and *Obeliscoides cuniculi* of *Obeliscoides* spp.
(7) Strongylida nematodes
(a) Nematodes of the Chabertiidae family, for example, *Chabertia ovina* of *Chabertia* spp.; and *Oesophagostomum brevicaudatum, Oesophagostomum columbianum, Oesophagostomum dentatum, Oesophagostomum georgianum, Oesophagostomum maplestonei, Oesophagostomum quadrispinulatum, Oesophagostomum radiatum, Oesophagostomum venulosum* and *Oesophagostomum watanabei* of *Oesophagostomum* spp.;
(b) Nematodes of the Stephanuridae family, for example, *Stephanurus dentatus* of *Stephanurus* spp.; and
(c) Nematodes of the Strongylidae family, for example, *Strongylus asini, Strongylus edentatus, Strongylus equinus* and *Strongylus vulgaris* of *Strongylus* spp.
(8) Oxyurida nematodes
Nematodes of the Oxyuridae family, for example, *Enterobius anthropopitheci* and *Enterobius vermicularis* of *Enterobius* spp.; *Oxyuris equi* of *Oxyuris* spp.; and *Passalurus ambiguus* of *Passalurus* spp.
(9) Ascaridida nemtaodes
(a) Nematodes of the Ascaridiidae family, for example, *Ascaridia galli* of *Ascaridia* spp.;
(b) Nematodes of the Heterakidae family, for example, *Heterakis beramporia, Heterakis brevispiculum, Heterakis gallinarum, Heterakis pusilla* and *Heterakis putaustralis* of *Heterakis* spp.;
(c) Nematodes of the Anisakidae family, for example, *Anisakis simplex* of *Anisakis* spp.;
(d) Nematodes of the Ascarididae family, for example, *Ascaris lumnbricoides* and *Ascaris suum* of *Ascaris* spp.; and *Parascaris equorum* of *Parascaris* spp.; and
(e) Nematodes of the Toxocaridae family, for example, *Toxocara canis, Toxocara leonina, Toxocarasuum, Toxocara vitulorum* and *Toxocara cati* of *Toxocara* spp.
(10) Spirurida nematodes
(a) Nematodes of the Onchocercidae family, for example, *Brugia malayi, Brugia pahangi* and *Brugia patei* of *Brugia* spp.; *Dipetalonema reconditum* of *Dipetalonema* spp.; *Dirofilaria immitis* of *Dirofilaria* spp.; *Filaria oculi* of *Filaria* spp.; and *Onchocerca cervicalis, Onchocerca gibsoni* and *Onchocerca gutturosa* of *Onchocerca* spp.
(b) Nematodes of the Setariidae family, for example, *Setaria digitata, Setaria equina, Setaria labiatopapillosa* and *Setaria marshalli* of *Setaria* spp.; and *Wuchereria bancrofti* of *Wuchereria* spp.; and
(c) Nematodes of the Filariidae family, for example, *Parafilaria multipapillosa* of *Parafilaria* spp.; and *Stephanofilaria assamensis, Stephanofilaria dedoesi, Stephanofilaria kaeli, Stephanofilaria okinawaensis* and *Stephanofilaria stilesi* of *Stephanofilaria* spp.
(11) Spirurida nematodes
(a) Nematodes of the Gnathostomatidae family, for example, *Gnathostoma doloresi* and *Gnathostoma spinigerum* of *Gnathostoma* spp.;
(b) Nematodes of the Habronematidae family, for example, *Habronema majus, Habronema microstoma* and *Habronema muscae* of *Habronema* spp.; and *Draschia megastoma* of *Draschia* spp.;
(c) Nematodes of the Physalopteridae family, for example, *Physaloptera canis, Physaloptera cesticillata, Physaloptera erdocyona, Physaloptera felidis, Physaloptera gemina, Physaloptera papilloradiata, Physaloptera praeputialis, Physaloptera pseudopraerutialis, Physaloptera rara, Physaloptera sibirica* and *Physaloptera vulpineus* of *Physaloptera* spp.;
(d) Nematodes of the Gongylonematidae family, for example, *Gongylonema pulchrum* of *Gongylonema* spp.;
(e) Nematodes of the Spirocercidae family, for example, *Ascarops strongylina* of *Ascarops* spp.; and
(f) Nematodes of the Thelaziidae family, for example, *Thelazia callipaeda, Thelazia gulosa, Thelazia lacrymalis, Thelazia rhodesi* and *Thelazia skrjabini* of *Thelazia* spp.

[Control Agent for Other Pests]

In addition, the pest control agent of the present invention exhibits an excellent control effect on other pests that have a sting or venom that can harm humans and animals, pests carrying various pathogens and pathogenic bacteria, and pests that impart discomfort to humans (such as toxic pests, sanitary insect pests, unpleasant insect pests).

Specific examples of these other pests are listed below.
(1) Hymenoptera insect pests Sawflies of the Argidae family, wasps of the Cynipidae family, sawflies of the Diprionidae family, ants of the Formicidae family, wasps of the Mutillidae vamily family, and wasps of the Vespidae family.
(2) Other insect pests Blattodea, termites, Araneae, centipedes, millipedes, crustacea and Cimex lectularius.

EXAMPLES

[Formulations]

Several examples of formulations of the pest control agent, insecticide, miticide, nematicide, endoparasite control agent or parasiticide of the present invention are described below, but the additives and the addition ratios are not limited to those detailed in these examples, and can be modified over a wide range. The units "parts" in the formulations indicate "parts by weight".

Formulations for agricultural and horticultural use and formulations for paddy rice are described below.
(Formulation 1: Water-Dispersible Powder)

Forty parts of the sufonylaminobenzamide compound of the present invention, 53 parts of diatomaceous earth, 4 parts of a higher alcohol sulfate and 3 parts of an alkylnaphthalene sulfonate salt were mixed together uniformly and then finely crushed to obtain a water-dispersible powder containing 40% of the active constituent.
(Formulation 2: Emulsion)

Thirty parts of the sufonylaminobenzamide compound of the present invention, 33 parts of xylene, 30 parts of dimethylformamide and 7 parts of a polyoxyethylene alkyl aryl ether were mixed together and dissolved to obtain an emulsion containing 30% of the active constituent.
(Formulation 3: Granules)

Five parts of the sufonylamninobenzamide compound of the present invention, 40 parts of talc, 38 parts of clay, 10 parts of bentonite and 7 parts of sodium alkyl sulfate were mixed together uniformly and then finely crushed, and the resulting powder was granulated into a granular shape having a diameter of 0.5 to 1.0 mm to obtain granules containing 5% of the active constituent.
(Formulation 4: Granules)

Five parts of the sufonylaminobenzamide compound of the present invention, 73 parts of clay, 20 parts of bentonite, 1 part of sodium dioctylsulfosuccinate and 1 part of potassium phosphate were thoroughly crushed and mixed together, water was then added to the resulting powder and thoroughly mixed, and the mixture was granulated and dried to obtain granules containing 5% of the active constituent.
(Formulation 5: Suspension)

Ten parts of the sufonylaminobenzamide compound of the present invention, 4 parts of a polyoxyethylene alkyl aryl ether, 2 parts of sodium polycarboxylate, 10 parts of glycerol, 0.2 parts of xanthan gum and 73.8 parts of water were mixed, and the resulting mixture was subjected to wet crushing down to a grain size of not more than 3 microns to obtain a suspension containing 10% of the active constituent.

Formulations for endoparasite control and formulations for parasiticides are described below.
(Formulation 6: Granulated Powder)

Five parts of the sufonylaminobenzamide compound of the present invention was dissolved in an organic solvent to obtain a solution, the solution was sprayed onto 94 parts of kaolin and 1 part of white carbon, and the solvent was then evaporated under reduced pressure. This type of granulated powder can be mixed with animal feed.
(Formulation 7: Injection)

From 0.1 to 1 part of the sufonylaminobenzamide compound of the present invention and 99 to 99.9 parts of peanut oil were mixed together uniformly, and the resulting mixture was then filter-sterilized using a sterilizing filter.
(Formulation 8: Pour-on Agent)

Five parts of the sufonylaminobenzamide compound of the present invention, 10 parts of a myristate ester and 85 parts of isopropanol were mixed together uniformly to obtain a pour-on agent.
(Formulation 9: Spot-on Agent)

From 10 to 15 parts of the sufonylaminobenzamide compound of the present invention, 10 parts of a palmitate ester and 75 to 80 parts of isopropanol were mixed together uniformly to obtain a spot-on agent.
(Formulation 10: Spray-on Agent)

One part of the sufonylaminobenzamide compound of the present invention, 10 parts of propylene glycol and 89 parts of isopropanol were mixed together uniformly to obtain a spray-on agent.

Examples of the compound are described below in order to describe the present invention in more detail. However, the present invention is in no way limited by the example compounds presented below.

Example 1

Synthesis of 4-(trifluoromethyl)-N-[4-(trifluoromethyl)phenyl]-2-(trifluoromethylsulfonylamino)benzamide (Compound Number: a-9)

Step 1

Synthesis of methyl 2-amino-4-(trifluoromethyl)benzoate

[Chemical formula 5]

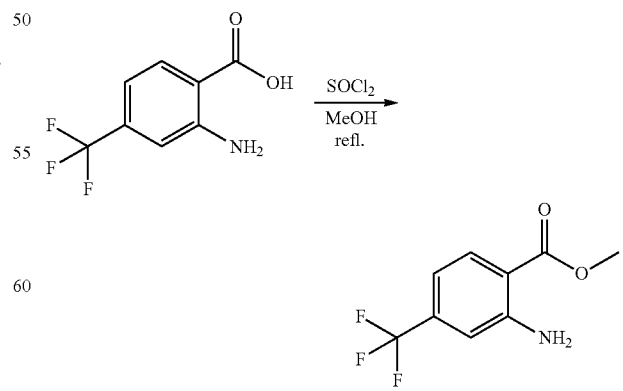

First, 4.10 g of 2-amino-4-(trifluoromethyl)benzoic acid was dissolved in 70 ml of methanol, and 12 ml of thionyl chloride was then added dropwise to the solution at 0° C. The temperature was then raised, and the reaction mixture was stirred for 12 hours under reflux conditions. After cooling to room temperature, the reaction solution was concentrated under reduced pressure, and the residue was dissolved in water and ethyl acetate. The resulting organic phase was washed with a saturated solution of sodium bicarbonate, dried over anhydrous magnesium sulfate, and then filtered. The filtrate was then concentrated under reduced pressure to obtain 3.70 g (yield: 85%) of the target product.

The ¹H-NMR of the obtained target product is shown below.

¹H-NMR (400 MHz, CDCl₃): δ 7.94 (d, 1H), 6.89 (s, 1H), 6.83 (d, 1H), 5.90 (brs, 2H), 3.89 (s, 3H).

Step 2

Synthesis of methyl 4-(trifluoromethyl)-2-(trifluoromethyl sulfonylamino)benzoate

[Chemical formula 6]

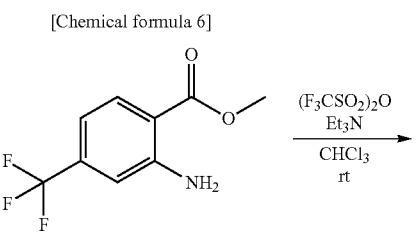

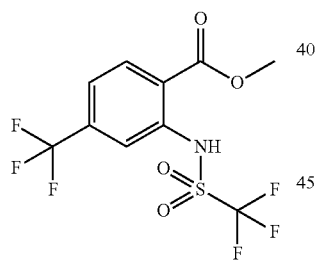

First, 4.92 g of methyl 2-amino-4-(trifluoromethyl)benzoate and 4.55 g of triethylamine were dissolved in 75 ml of chloroform, and 12.7 g of trifluoromethanesulfonic anhydride was then added dropwise to the solution at 0° C. The temperature was then raised to room temperature, and the reaction solution was stirred for 7 hours. The reaction solution was then poured into water and extracted with chloroform. The thus obtained organic phase was washed with a saturated solution of sodium bicarbonate, dried over anhydrous magnesium sulfate, and then filtered. The filtrate was then concentrated under reduced pressure, and the obtained residue was purified by silica gel column chromatography to obtain 5.80 g (yield: 74%) of the target product.

The ¹H-NMR of the obtained target product is shown below.

¹H-NMR (400 MHz, CDCl₃): δ 11.37 (s, 1H), 8.19 (d, 1H), 8.02 (s, 1H), 7.46 (d, 1H), 3.98 (s, 3H).

Step 3

Synthesis of 4-(trifluoromethyl)-2-(trifluoromethyl-sulfonylamino)benzoic acid

[Chemical formula 7]

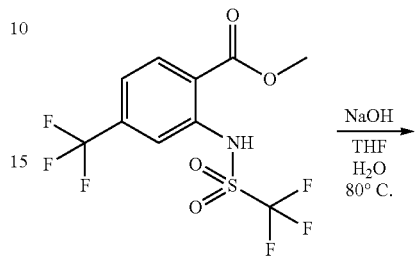

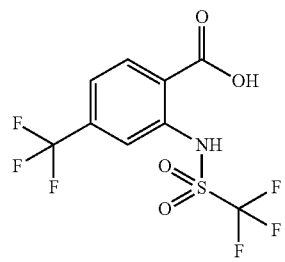

First, 5.80 g of methyl 4-(trifluoromethyl)-2-(trifluoromethylsulfonylamino)benzoate was dissolved in 30 ml of tetrahydrofuran, and 13 ml of a 4N aqueous solution of sodium hydroxide was added at room temperature. The temperature was then raised to 80° C., and the reaction solution was stirred for 2 hours. After cooling to room temperature, the reaction solution was poured into water, and diethyl ether was added to achieve a phase separation. Dilute hydrochloric acid was added to the obtained aqueous phase under cooling to produce an acidic state, and an extraction was then performed with ethyl acetate. The thus obtained organic phase was washed with a saturated saline solution, dried over anhydrous magnesium sulfate, and then filtered. The filtrate was then concentrated under reduced pressure to obtain 4.56 g (yield: 82%) of the target product.

The ¹H-NMR of the obtained target product is shown below.

¹H-NMR (400 MHz, DMSO-d₆): δ 8.08 (d, 1H), 7.85 (s, 1H), 7.40 (d, 1H)

Step 4

Synthesis of 4-(trifluoromethyl)-N-[4-(trifluoromethyl)phenyl]-2-(trifluoromethylsulfonylamino)benzamide

[Chemical formula 8]

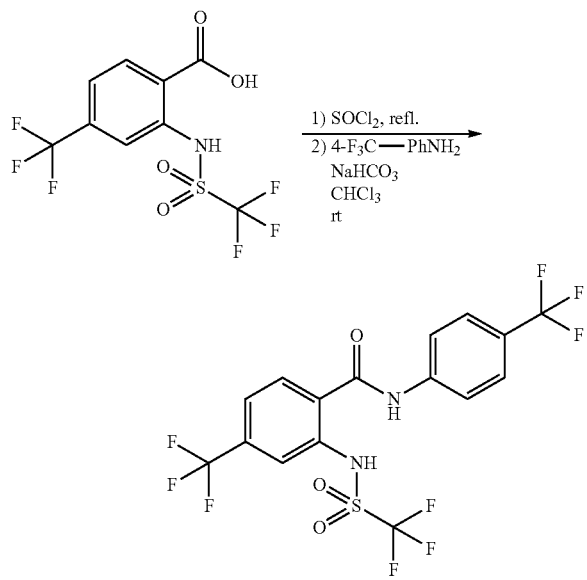

First, 0.40 g of 4-(trifluoromethyl)-2-(trifluoromethylsulfonylamino)benzoic acid was dissolved in 4 ml of thionyl chloride, and the solution was stirred for 2 hours under reflux conditions. The reaction solution was then concentrated under reduced pressure, and the residue was dissolved in 15 ml of chloroform. Subsequently, 0.23 g of 4-trifluoromethylaniline was added at 0° C., and 0.30 g of sodium bicarbonate was then added. The temperature as then raised to room temperature, and the reaction mixture was stirred for 3 hours. The reaction mixture was then concentrated under reduced pressure, and the residue was dissolved in water and ethyl acetate. The thus obtained organic phase was washed with a saturated saline solution, dried over anhydrous magnesium sulfate, and then filtered. The filtrate was then concentrated under reduced pressure, and the obtained residue was purified by silica gel column chromatography to obtain 0.44 g (yield: 77%) of the target product.

The $^1$H-NMR of the obtained target product is shown below.

$^1$H-NMR (400 MHz, DMSO-$d_6$): δ 13.50 (s, 1H), 8.21 (d, 1H), 7.86 (s, 1H), 7.81 (d, 2H), 7.71 (d, 2H), 7.23 (d, 1H).

A part of compounds of the present invention produced using a similar method to the example described above are shown in Table 1 to Table 2. Table 1 shows the substituents in compounds represented by formula (I-1). Table 2 shows the substituents in compounds represented by formula (I-2). The physical state or melting point (m.p.) is also shown in the tables to indicate the physical property of each compound. In the tables, Me represents a methyl group, Et represents an ethyl group, and $^i$Pr represents an isopropyl group.

[Chemical formula 9]

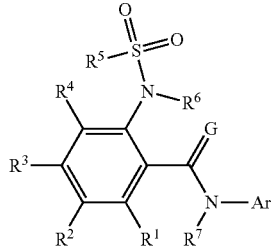

(I-1)

TABLE 1

| Compound number | R$^1$ | R$^2$ | R$^3$ | R$^4$ | R$^5$ | R$^6$ | R$^7$ | G | Ar | Physical property |
|---|---|---|---|---|---|---|---|---|---|---|
| a-1 | H | H | Cl | H | CF$_3$ | H | H | O | 3,5-(CF$_3$)$_2$-phenyl | amorphous |
| a-2 | H | H | CF$_3$ | H | CF$_3$ | H | H | O | 3-CF$_3$-4-F-phenyl | m.p. 187-189° C. |
| a-3 | H | H | CF$_3$ | H | CF$_3$ | H | H | O | 3,5-(CF$_3$)$_2$-phenyl | amorphous |
| a-4 | H | H | CF$_3$ | H | CF$_3$ | H | H | O | 4-CF$_3$-phenyl | m.p. 212-214° C. |
| a-5 | H | H | Cl | H | CF$_3$ | H | Me | O | 3,5-(CF$_3$)$_2$-phenyl | m.p. 148-150° C. |
| a-6 | H | H | F | H | CF$_3$ | H | H | O | 3,5-(CF$_3$)$_2$-phenyl | amorphous |
| a-7 | H | H | CF$_3$ | H | CF$_3$ | H | H | O | 2-Cl-4-CF$_3$-phenyl | m.p. 180-182° C. |
| a-8 | H | H | CF$_3$ | H | CF$_3$ | H | H | O | 5-CF$_3$-pyridin-2-yl | m.p. 220° C. up |
| a-9 | H | H | CF$_3$ | H | CF$_3$ | H | H | O | 3-F-5-CF$_3$-phenyl | m.p. 179-181° C. |
| a-10 | H | H | CF$_3$ | H | CF$_3$ | H | H | O | 3-Cl-4-CF$_3$-phenyl | m.p. 203-205° C. |
| a-11 | H | H | CF$_3$ | H | CF$_3$ | H | H | O | 2-F-5-CF$_3$-phenyl | m.p. 172-174° C. |
| a-12 | H | H | CF$_3$ | H | CF$_3$ | H | H | O | 3-OCF$_3$-phenyl | amorphous |
| a-13 | H | H | CF$_3$ | H | CF$_3$ | H | H | O | 4-Me-phenyl | m.p. 192-194° C. |
| a-14 | H | H | CF$_3$ | H | CF$_3$ | H | H | O | 4-Cl-phenyl | m.p. 198-200° C. |
| a-15 | H | H | CF$_3$ | H | CF$_3$ | H | H | O | 4-OCF$_3$-phenyl | amorphous |
| a-16 | H | F | F | H | CF$_3$ | H | H | O | 3-CF$_3$-4-F-phenyl | m.p. 172-174° C. |
| a-17 | H | H | Me | H | CF$_3$ | H | H | O | 3-CF$_3$-4-F-phenyl | m.p. 176-178° C. |
| a-18 | H | H | CF$_3$ | H | CF$_3$ | H | H | O | 2,6-Cl$_2$-4-CF$_3$-phenyl | m.p. 194-195° C. |
| a-19 | H | H | CF$_3$ | H | CF$_3$ | H | H | O | 5-(1,1,1,3,3,3-hexafluoropropan-2-yl)thiazol-2-yl | m.p. 220° C. up |
| a-20 | H | H | CF$_3$ | H | CF$_3$ | H | H | O | 2-Me-4-(perfluoropropan-2-yl)-phenyl | m.p. 188-190° C. |
| a-21 | H | H | CF$_3$ | H | CF$_3$ | Me | H | O | 3-CF$_3$-4-F-phenyl | m.p. 178-179° C. |
| a-22 | H | H | CF$_3$ | H | CF$_3$ | H | H | O | 3,4-Cl$_2$-phenyl | m.p. 193-195° C. |
| a-23 | H | H | CF$_3$ | H | CF$_3$ | H | H | O | 3-Cl-5-CF$_3$-pyridin-2-yl | m.p. 220° C. up |

TABLE 1-continued

| Compound number | R¹ | R² | R³ | R⁴ | R⁵ | R⁶ | R⁷ | G | Ar | Physical property |
|---|---|---|---|---|---|---|---|---|---|---|
| a-24 | H | H | OCF₃ | H | CF₃ | H | H | O | 4-OCF₃-phenyl | m.p. 172-175° C. |
| a-25 | H | H | OCF₃ | H | CF₃ | H | H | O | 3-CF₃-4-F-phenyl | m.p. 165-168° C. |
| a-26 | H | H | OCF₃ | H | CF₃ | H | H | O | 4-CF₃-phenyl | m.p. 176-179° C. |
| a-27 | H | H | CF₃ | H | CF₃ | Me | H | O | 4-OCF₃-phenyl | m.p. 167-168° C. |
| a-28 | H | H | CF₃ | H | CF₃ | H | H | O | 4-SF₅-phenyl | m.p. 220-222° C. |
| a-29 | H | H | Br | H | CF₃ | H | H | O | 4-OCF₃-phenyl | amorphous |
| a-30 | H | H | CF₃ | H | CH₂CF₃ | H | H | O | 4-OCF₃-phenyl | m.p. 185-188° C. |
| a-31 | H | H | 1H-1,2,4-triazol-1-yl | H | CF₃ | H | H | O | 4-OCF₃-phenyl | m.p. 220° C. up |
| a-32 | H | H | 6-Cl-pyridin-3-yl | H | CF₃ | H | H | O | 4-OCF₃-phenyl | m.p. 199-201° C. |
| a-33 | H | H | CF₃ | H | CHF₂ | H | H | O | 4-OCF₃-phenyl | m.p. 127-129° C. |
| a-34 | H | H | 6-CF₃-pyridin-3-yl | H | CF₃ | H | H | O | 4-OCF₃-phenyl | m.p. 170-172° C. |
| a-35 | H | H | 4-CF₃-phenyl | H | CF₃ | H | H | O | 4-OCF₃-phenyl | m.p. 152-154° C. |
| a-36 | H | H | CN | H | CF₃ | H | H | O | 4-CF₃-phenyl | amorphous |
| a-37 | H | H | CF₃ | H | CF₃ | H | H | O | 3-CF₃-4-CN-phenyl | m.p. 220° C. up |
| a-38 | H | H | CN | H | CH₂CF₃ | H | H | O | 4-CF₃-phenyl | m.p. 220° C. up |
| a-39 | H | H | CF₃ | H | CF₃ | H | H | O | 4-CN-phenyl | m.p. 220° C. up |
| a-40 | H | H | CN | H | CF₃ | H | H | O | 4-CN-phenyl | m.p. 220° C. up |
| a-41 | H | H | Cl | H | CF₃ | H | H | O | 3-CF₃-4-F-phenyl | amorphous |
| a-42 | H | H | 2-Cl-4-CF₃-phenyl | H | CF₃ | H | H | O | 4-OCF₃-phenyl | amorphous |
| a-43 | H | H | CF₃ | H | CF₃ | H | H | O | 4-SCF₃-phenyl | m.p. 185-187° C. |
| a-44 | H | H | CF₃ | H | CF₃ | H | H | O | 3-(1H-1,2,4-triazol-1-yl)phenyl | m.p. 220° C. up |
| a-45 | H | H | CF₃ | H | CF₃ | H | H | O | 4-(3-Me-1,2,4-oxadiazol-5-yl)phenyl | m.p. 220° C. up |
| a-46 | H | H | CF₃ | H | CF₃ | H | H | O | 4-(5-Me-1,3,4-oxadiazol-2-yl)phenyl | m.p. 220° C. up |
| a-47 | H | H | CF₃ | H | CF₃ | H | H | O | pyridin-3-yl | m.p. 220° C. up |
| a-48 | H | H | CF₃ | H | CF₃ | H | H | O | pyridin-4-yl | m.p. 220° C. up |
| a-49 | H | H | CF₃ | H | CF₃ | H | H | O | 2-COOMe-4-Br-phenyl | m.p. 220° C. up |
| a-50 | H | H | CF₃ | H | CF₃ | H | H | O | 4-NO₂-phenyl | m.p. 220° C. up |
| a-51 | H | H | CF₃ | H | CF₃ | H | H | O | 2-CN-4-Cl-phenyl | m.p. 230° C. up |
| a-52 | H | H | CF₃ | H | CF₃ | H | H | O | 2-CONHMe-4-Cl-phenyl | m.p. 230° C. up |
| a-53 | H | H | CF₃ | H | CF₃ | H | H | O | 2-F-4-CN-phenyl | m.p. 230° C. up |
| a-54 | H | H | CF₃ | H | CF₃ | H | H | O | 2-F-4-CF₃-phenyl | amorphous |
| a-55 | H | H | CF₃ | H | CF₃ | H | H | O | 2-CF₃-4-Cl-phenyl | amorphous |
| a-56 | H | H | CF₃ | H | CF₃ | H | H | O | 2-OCH₂CF₃-pyridin-4-yl | amorphous |
| a-57 | H | H | CF₃ | H | CF₃ | H | H | O | 2-COOMe-4-F-phenyl | m.p. 135-137° C. |
| a-58 | H | H | CF₃ | H | CF₃ | H | H | O | 2-COOMe-4-CF₃-phenyl | m.p. 127-130° C. |
| a-59 | H | H | CF₃ | H | CF₃ | H | H | O | 2-OEt-4-CF₃-phenyl | m.p. 220° C. up |
| a-60 | H | H | CF₃ | H | CF₃ | H | H | O | 2-COOMe-4-Cl-phenyl | m.p. 220° C. up |
| a-61 | H | H | CF₃ | H | CF₃ | H | H | O | 2-COOEt-4-Br-phenyl | m.p. 195-197° C. |
| a-62 | H | H | CF₃ | H | CF₃ | H | H | O | 2-COOMe-4-I-phenyl | m.p. 220° C. up |
| a-63 | H | H | CF₃ | H | CF₃ | H | H | O | 2-COOMe-5-CF₃-phenyl | m.p. 132-134° C. |
| a-64 | H | H | CF₃ | H | CF₃ | H | H | O | 3-F-4-CF₃-phenyl | amorphous |
| a-65 | H | H | CF₃ | H | CF₃ | H | H | O | 2-COOⁱPr-4-Br-phenyl | m.p. 142-144° C. |
| a-66 | H | H | CF₃ | H | CF₃ | H | H | O | 2-COEt-4-CF₃-phenyl | m.p. 105-107° C. |
| a-67 | H | H | CF₃ | H | CF₃ | H | H | O | 2-COOMe-4-CN-phenyl | m.p. 218-220° C. |
| a-68 | H | H | CF₃ | H | CF₃ | H | H | O | 2-Cl-4-Br-phenyl | m.p. 181-183° C. |
| a-69 | H | H | CF₃ | H | CF₃ | H | H | O | 3-Cl-4-Br-phenyl | amorphous |
| a-70 | H | H | CF₃ | H | CF₃ | H | H | O | 3-CF₃-4-Cl-phenyl | amorphous |
| a-71 | H | H | CF₃ | H | CF₃ | H | H | O | 2-COOMe-4,6-Cl₂-phenyl | amorphous |
| a-72 | H | H | CF₃ | H | CF₃ | H | H | O | 3-COOMe-4-Cl-phenyl | m.p. 217-219° C. |
| a-73 | H | H | Br | H | CF₃ | H | H | O | 2-COOMe-4-Br-phenyl | m.p. 171-173° C. |
| a-74 | H | H | CF₃ | H | CF₃ | H | H | O | 4-Br-2-(4,5-dihydrooxazol-2-yl)-phenyl | m.p. 220° C. up |
| a-75 | H | H | CF₃ | H | CF₃ | H | H | O | 2-COOMe-4-NO₂-phenyl | m.p. 174-176° C. |
| a-76 | H | H | CF₃ | H | CF₃ | H | H | O | 4-Br-2-(1H-pyrazol-1-yl)-phenyl | m.p. 151-153° C. |
| a-77 | H | H | CF₃ | H | CF₃ | H | H | O | 2-SO₂Me-4-Br-phenyl | m.p. 215-217° C. |
| a-78 | H | H | CF₃ | H | CF₃ | H | H | O | 2-COOMe-4,5-F₂-phenyl | m.p. 177-180° C. |
| a-79 | H | H | CF₃ | H | CF₃ | H | H | O | 2-COOMe-4-I-5-Cl-phenyl | m.p. 170-172° C. |
| a-80 | H | H | CF₃ | H | CF₃ | H | H | O | 2-COOMe-4,5-Cl₂-phenyl | m.p. 154-156° C. |
| a-81 | H | H | CF₃ | H | CF₃ | H | H | O | 5-CF₃-2-(1H-pyrazol-1-yl)-phenyl | m.p. 164-167° C. |
| a-82 | H | H | CF₃ | H | CF₃ | H | H | O | 2-COOMe-4-CF₃-5-Cl-phenyl | m.p. 172-174° C. |
| a-83 | H | H | CF₃ | H | CF₃ | H | H | O | 2-COOMe-4-Br-5-Cl-phenyl | m.p. 163-165° C. |
| a-84 | H | CF₃ | Cl | H | CF₃ | H | H | O | 2-COOMe-4-Br-phenyl | m.p. 220° C. up |
| a-85 | H | H | CF₃ | H | CF₃ | H | H | O | 2-COOMe-4-Br-5-F-phenyl | m.p. 163-165° C. |
| a-86 | H | H | CF₃ | H | CF₃ | H | H | O | 2-COOMe-4-CF₃-5-F-phenyl | m.p. 170-172° C. |
| a-87 | H | F | F | H | CF₃ | H | H | O | 2-COOMe-4,5-F₂-phenyl | m.p. 220° C. up |
| a-88 | H | Br | Cl | H | CF₃ | H | H | O | 2-COOMe-4,5-F₂-phenyl | m.p. 220° C. up |
| a-89 | H | H | CF₃ | H | CF₃ | H | H | O | 2-COOMe-5-NO₂-phenyl | m.p. 163-165° C. |
| a-90 | H | H | CF₃ | H | CF₃ | H | H | O | 2-COOMe-4-Cl-5-F-phenyl | m.p. 220° C. up |
| a-91 | H | H | NO₂ | H | CF₃ | H | H | O | 2-COOMe-4,5-F₂-phenyl | m.p. 220-222° C. |

TABLE 1-continued

| Compound number | R¹ | R² | R³ | R⁴ | R⁵ | R⁶ | R⁷ | G | Ar | Physical property |
|---|---|---|---|---|---|---|---|---|---|---|
| a-92 | H | H | $CF_3$ | H | $CF_3$ | H | H | O | 2-COOMe-5-Cl-phenyl | m.p. 131-133° C. |
| a-93 | H | F | F | H | $CF_3$ | H | H | O | 2-COOMe-5-$CF_3$-phenyl | m.p. 125-128° C. |
| a-94 | H | H | $CF_3$ | H | $CF_3$ | H | H | O | 2-COOMe-5-F-phenyl | m.p. 198-200° C. |
| a-95 | H | H | $CF_3$ | H | $CF_3$ | H | H | O | 6-Cl-4-COOMe-pyridin-3-yl | m.p. 168-170° C. |
| a-96 | H | H | $CF_3$ | H | $CF_3$ | H | H | O | 2-Cl-5-COOMe-pyridin-4-yl | m.p. 183-185° C. |
| a-97 | H | Cl | Cl | H | $CF_3$ | H | H | O | 2-COOMe-4,5-$F_2$-phenyl | m.p. 220° C. up |
| a-98 | H | F | $CF_3$ | H | $CF_3$ | H | H | O | 2-COOMe-4,5-$F_2$-phenyl | m.p. 220° C. up |
| a-99 | H | $CF_3$ | F | H | $CF_3$ | H | H | O | 2-COOMe-4,5-$F_2$-phenyl | m.p. 220° C. up |
| a-100 | H | H | 6-$CF_3$-pyridin-3-yl | H | $CF_3$ | H | H | O | 2-COOMe-4,5-$F_2$-phenyl | m.p. 195-197° C. |
| a-101 | H | H | $CF_3$ | H | $CF_3$ | H | H | O | 5-$CF_3$-2-(1H-1,2,4-triazol-1-yl)-phenyl | m.p. 220° C. up |
| a-102 | H | H | $CF_3$ | H | $CF_3$ | H | H | O | 2-COOMe-4-Br-6-F-phenyl | m.p. 178-180° C. |
| a-103 | H | H | $CF_3$ | H | $CF_3$ | H | H | O | 2-$NO_2$-4-$CF_3$-phenyl | m.p. 177-179° C. |
| a-104 | H | H | $CF_3$ | H | $CF_3$ | H | H | O | 2-COOMe-3-Cl-phenyl | m.p. 181-184° C. |
| a-105 | H | H | $CF_3$ | H | $CF_3$ | H | H | O | 2-COOMe-4,6-$F_2$-phenyl | m.p. 152-154° C. |
| a-106 | H | H | $CF_3$ | H | $CF_3$ | H | H | O | 2-COOMe-4,5,6-$F_3$-phenyl | m.p. 160-162° C. |
| a-107 | H | H | $CF_3$ | H | $CF_3$ | H | H | O | 2-COOMe-3,4,5,6-$F_4$-phenyl | m.p. 182-184° C. |
| a-108 | H | H | $CF_3$ | H | $CF_3$ | H | H | O | 2-$NO_2$-4,5-$F_2$-phenyl | m.p. 158-161° C. |
| a-109 | H | H | $CF_3$ | H | $CF_3$ | H | H | O | 2-COOMe-4-$OCF_3$-phenyl | m.p. 210-212° C. |
| a-110 | H | F | F | H | $CF_3$ | H | H | O | 2-COOMe-4-$OCF_3$-phenyl | m.p. 127-129° C. |
| a-111 | H | F | F | H | $CF_3$ | H | H | O | 2-COOMe-4-$CF_3$-phenyl | m.p. 128-130° C. |
| a-112 | H | Br | Cl | H | $CF_3$ | H | H | O | 2-COOMe-4-$CF_3$-phenyl | m.p. 220° C. up |
| a-113 | H | F | F | H | $CF_3$ | H | H | O | 2-COOMe-4-$NO_2$-phenyl | m.p. 220° C. up |
| a-114 | H | H | $CF_3$ | H | $CF_3$ | H | H | O | 2-COOMe-3-Cl-4-Br-phenyl | m.p. 208-210° C. |
| a-115 | H | H | $CF_3$ | H | $CF_3$ | H | H | O | 2-(CH=NOMe)-4-Cl-phenyl | m.p. 220° C. up |
| a-116 | H | H | $CF_3$ | H | $CF_3$ | H | H | O | 2,4,5-$F_3$-phenyl | m.p. 185-187° C. |
| a-117 | H | H | Cl | H | $CF_3$ | H | H | O | 2-COOMe-4,5-$F_2$-phenyl | m.p. 156-158° C. |
| a-118 | H | H | 6-$CF_3$-pyridin-3-yl | H | $CF_3$ | H | H | O | 4-$CF_3$-phenyl | m.p. 220-223° C. |
| a-119 | H | H | 6-$CF_3$-pyridin-3-yl | H | $CF_3$ | H | H | O | 3-F-4-$CF_3$-phenyl | m.p. 220° C. up |
| a-120 | H | H | 6-$CF_3$-pyridin-3-yl | H | $CF_3$ | H | H | O | 3-$CF_3$-4-F-phenyl | m.p. 213-215° C. |
| a-121 | H | H | 6-$CF_3$-pyridin-3-yl | H | $CF_3$ | H | H | O | 4-$NO_2$-phenyl | m.p. 220° C. up |
| a-122 | H | $CF_3$ | F | H | $CF_3$ | H | H | O | 4-$CF_3$-phenyl | m.p. 220° C. up |
| a-123 | H | F | $CF_3$ | H | $CF_3$ | H | H | O | 4-$CF_3$-phenyl | amorphous |
| a-124 | H | Br | Cl | H | $CF_3$ | H | H | O | 4-$CF_3$-phenyl | m.p. 220° C. up |
| a-125 | H | H | $CF_3$ | H | $CF_3$ | H | H | O | 3-COOMe-thiophen-2-yl | m.p. 210-213° C. |
| a-126 | H | H | $CF_3$ | H | $CF_3$ | H | H | O | 2-COOMe-3-F-4-Br-phenyl | m.p. 185-187° C. |
| a-127 | H | F | F | H | $CF_3$ | H | H | O | 4-$CF_3$-phenyl | amorphous |
| a-128 | H | Cl | Cl | H | $CF_3$ | H | H | O | 4-$CF_3$-phenyl | amorphous |
| a-129 | H | Cl | F | H | $CF_3$ | H | H | O | 4-$CF_3$-phenyl | amorphous |
| a-130 | H | H | $CF_3$ | H | $CF_3$ | H | H | O | 2-NHCOMe-5-$CF_3$-phenyl | m.p. 220° C. up |
| a-131 | H | Br | Cl | H | $CF_3$ | H | H | O | 2-COOMe-5-$CF_3$-phenyl | m.p. 160-162° C. |
| a-132 | H | Cl | Br | H | $CF_3$ | H | H | O | 2-COOMe-4,5-$F_2$-phenyl | m.p. 220° C. up |
| a-133 | H | H | $CF_3$ | H | $CF_3$ | H | H | O | 2-COMe-4-Br-phenyl | m.p. 151-153° C. |
| a-134 | H | H | $CF_3$ | H | $CF_3$ | H | H | O | 2-COMe-5-$CF_3$-phenyl | m.p. 113-115° C. |
| a-135 | H | H | $CF_3$ | H | $CF_3$ | H | H | O | 2-(1H-pyrazol-1-yl)-4-$CF_3$-phenyl | m.p. 223-225° C. |
| a-136 | H | Br | Cl | H | $CF_3$ | H | H | O | 2-(1H-pyrazol-1-yl)-5-$CF_3$-phenyl | m.p. 199-202° C. |
| a-137 | H | Cl | F | H | $CF_3$ | H | H | O | 2-COOMe-5-$CF_3$-phenyl | m.p. 150-152° C. |
| a-138 | H | H | $CF_3$ | H | $CF_3$ | H | H | O | 3,4-$F_2$-phenyl | amorphous |
| a-139 | H | H | $CF_3$ | H | $CF_3$ | H | H | O | 2-(1,3,4-oxadiazol-2-yl)-5-$CF_3$-phenyl | m.p. 180-182° C. |
| a-140 | H | H | $CF_3$ | H | $CF_3$ | H | H | O | 2-(4,5-dihydrooxazol-2-yl)-5-$CF_3$-phenyl | m.p. 222-225° C. |
| a-141 | H | H | Cl | H | $CF_2CF_2CF_2CF_3$ | H | H | O | 3-$CF_3$-4-F-phenyl | amorphous |
| a-142 | H | H | $CF_3$ | H | $CF_2CF_2CF_2CF_3$ | H | H | O | 4-$OCF_3$-phenyl | amorphous |
| a-143 | H | Br | Cl | H | $CF_3$ | H | H | O | 3,4-$F_2$-phenyl | m.p. 227-229° C. |

[Chemical formula 10]

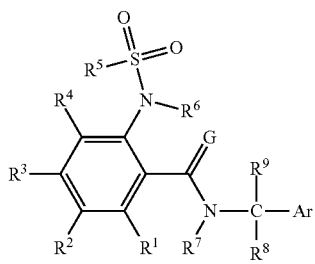

(I-2)

TABLE 2

| Compound number | R¹ | R² | R³ | R⁴ | R⁵ | R⁶ | R⁷ | R⁸ | R⁹ | G | Ar | Physical property |
|---|---|---|---|---|---|---|---|---|---|---|---|---|
| b-1 | H | H | $CF_3$ | H | $CF_3$ | H | H | H | H | O | 4-Cl-phenyl | m.p. 127-129° C. |
| b-2 | H | H | $CF_3$ | H | $CF_3$ | H | H | Me | Me | O | 4-Cl-phenyl | amorphous |
| b-3 | H | H | $CF_3$ | H | $CF_3$ | H | H | $^{i}Pr$ | H | O | 4-Cl-phenyl | m.p. 168-170° C. |
| b-4 | H | H | $CF_3$ | H | $CF_3$ | H | H | Me | H | O | 3-Cl-5-$CF_3$-pyridin-2-yl | amorphous |
| b-5 | H | H | $CF_3$ | H | $CF_3$ | H | H | Me | H | O | 5-$CF_3$-pyridin-2-yl | m.p. 163-165° C. |
| b-6 | H | H | $CF_3$ | H | $CF_3$ | H | H | Et | H | O | 5-$CF_3$-pyridin-2-yl | amorphous |

Among the compounds shown in Table 1 to Table 2, those compounds having a physical property described as "viscous oil" or "amorphous" were subjected to a $^1$H-NMR (DMSO-$d_6$) measurement. The measurement results are shown in Table 3.

TABLE 3

| Compound number | $^1$H-NMR (DMSO-$d_6$, δ ppm) |
|---|---|
| a-1 | 8.80 (brs, 1H), 8.19 (s, 2H), 8.02 (d, 1H), 7.75 (s, 1H), 7.53 (s, 1H), 7.00 (d, 1H) |
| a-3 | 8.21 (s, 2H), 8.18 (d, 1H), 7.82 (s, 1H), 7.77 (s, 1H), 7.24 (d, 1H) |
| a-6 | 8.80 (brs, 1H), 8.19 (s, 2H), 8.08 (m, 1H), 7.73 (s, 1H), 7.25 (d, 1H), 6.78 (m, 1H) |
| a-12 | 8.20 (d, 1H), 7.90 (s, 1H), 7.85 (s, 1H), 7.48 (t, 1H), 7.37 (d, 1H), 7.22 (d, 1H), 7.05 (d, 1H) |
| a-15 | 8.21 (d, 1H), 7.85 (s, 1H), 7.72 (d, 2H), 7.36 (d, 2H), 7.22 (d, 1H) |
| a-29 | 7.94 (d, 1H), 7.69 (m, 3H), 7.34 (d, 2H), 7.11 (d, 1H) |
| a-36 | 13.40 (s, 1H), 8.77 (bs, 1H), 8.17 (d, 1H), 7.83 (m, 3H), 7.79 (d, 2H), 7.33 (d, 1H) |
| a-41 | 13.40 (s, 1H), 8.21 (m, 1H), 8.02 (d, 1 H), 7.65 (m, 1H), 7.51 (m, 2H), 6.97 (d, 1 H) |
| a-42 | 13.20 (bs, 1H), 8.10 (d, 1H), 7.95 (s, 1H), 7.77 (m, 3H), 7.60 (d, 2H), 7.37 (d, 2H), 7.07 (d, 1H) |
| a-54 | 8.71 (t, 1H), 8.24 (d, 1H), 7.97 (s, 1H), 7.73 (d, 2H), 7.56 (d, 1H), 7.22 (d, 1H) |
| a-55 | 8.20 (d, 1H), 7.98 (d, 1H), 7.90 (s, 1H), 7.74 (m, 2H), 7.19 (d, 1H) |
| a-56 | 13.20 (s, 1H), 8.18 (d, 1H), 8.09 (d, 1H), 7.85 (s, 1H), 7.27 (m, 2H), 7.09 (d, 1H), 4.95 (m, 2H) |
| a-64 | 8.20 (d, 1H), 7.93 (d, 1H), 7.85 (s, 1H), 7.77 (t, 1H), 7.31 (d, 1H), 7.23 (d, 1H) |
| a-69 | 8.18 (d, 1H), 8.08 (d, 1H), 7.84 (s, 1H), 7.73 (d, 1H), 7.32 (m, 1H), 7.21 (d, 1H) |
| a-70 | 8.31 (s, 1H), 8.19 (d, 1H), 7.84 (s, 1H), 7.71 (m, 2H), 7.23 (d, 1H) |
| a-71 | 8.14 (d, 1H), 7.96 (s, 1H), 7.91 (d, 1H), 7.62 (d, 1H), 7.18 (m, 1H) |
| a-123 | 13.51 (s, 1H), 7.93 (d, 1H), 7.86 (d, 1H), 7.80 (d, 2H), 7.72 (d, 2H) |
| a-127 | 13.49 (s, 1H), 7.93 (d, 1H), 7.77 (d, 2H), 7.70 (d, 2H), 7.54 (m, 1H) |
| a-128 | 13.33 (s, 1H), 8.11 (s, 1H), 7.78 (d, 2H), 7.20 (m, 3H) |
| a-129 | 13.35 (s, 1H), 8.10 (d, 1H), 7.76 (d, 2H), 7.71 (d, 2H), 7.43 (d, 1H) |
| a-138 | 13.39 (s, 1H), 8.19 (d, 1H), 7.91 (m, 1H), 7.83 (s, 1H), 7.43 (m, 1H), 7.21 (d, 1H), 7.14 (m, 1 H) |
| a-141 | 13.38 (s, 1H), 8.17 (m, 1H), 8.01 (d, 1H), 7.65 (m, 1H), 7.61 (s, 1H), 7.53 (t, 1H), 7.97 (d, 1H) |
| a-142 | 13.30 (s, 1H), 8.20 (d, 1H), 7.93 (s, 1H), 7.71 (d, 2H), 7.36 (d, 2H), 7.22 (d, 1H) |
| b-2 | 11.12 (s, 1H), 7.97 (d, 1H), 7.83 (s, 1H), 7.30 (m, 4H), 7.09 (d, 1H) |
| b-4 | 11.12 (d, 1H), 8.81 (s, 1H), 8.37 (s, 1H), 8.03 (d, 1H), 7.79 (s, 1H), 7.12 (d, 1H), 5.55 (m, 1H), 1.42 (d, 3H) |
| b-6 | 11.08 (d, 1H), 8.88 (s, 1H), 8.10 (m, 1H), 8.03 (d, 1H), 7.89 (s, 1H), 7.54 (d, 1H), 7.15 (d, 1H), 5.03 (m, 1H), 1.95-1.87 (m, 2H), 0.91 (m, 3H) |

As described above, the sufonylaminobenzamide compound of the present invention can be produced easily by using known chemical reactions such as those described in the example above. The fact that compounds not specifically disclosed in the present description, namely compounds substituted with various substituents which do not depart from the object and scope of the present invention, can be produced and used in accordance with the methods described above or similar methods will be readily understood by those skilled in the art on the basis of the disclosure within the present description.

[Biological Testing]

The test examples described below demonstrate that the sufonylaminobenzanmide compound of the present invention (hereafter also referred to as "the compound of the present invention") is useful as the active constituent in a pest control agent. The units "parts" are based on weight.

(Preparation of Test Emulsion)

Five parts of the compound of the present invention, 93.6 parts of dimethylformamide and 1.4 parts of a polyoxyethylene alkyl aryl ether were mixed together and dissolved to obtain an emulsion (1) containing 5% of the active constituent.

The mortality rate was calculated using the following equation.

Mortality rate (%)=(number of dead pests/number of test pests)×100

(Test Example 1) Efficacy Test Against *Mythimna separata*

First, 0.8 g of an artificial feed (Insecta LFS, manufactured by Nosan Corporation) and 1 µl of the emulsion (I) were mixed thoroughly, and 0.2 g of the resulting mixture was placed in each of the treatment areas of a plastic test container (volume: 1.4 ml) to complete preparation of a test feed.

Two second-instar larvae of *Mythimna separata* were inoculated into each treatment area, and the test container was sealed with a plastic lid. The sealed container was placed in a temperature-controlled room at 25° C., and the mortality rate and the amount of feed consumed were determined on the fifth day. The test was repeated. Further, a test performed under the same conditions, but with the exception of excluding the compound of the present invention from the emulsion (1), was used as a control.

Efficacy tests against *Mythimna separata* were conducted for the compounds having the compound numbers shown in Table 4. For all of the compounds, the mortality rate against *Mythimna separata* was 100%, or the amount of feed consumed was 10% or less of the amount of feed consumed in the control.

TABLE 4

| a-1  | a-22 | a-41 | a-65 | a-86  | a-113 | a-133 |
|------|------|------|------|-------|-------|-------|
| a-2  | a-23 | a-42 | a-66 | a-87  | a-114 | a-134 |
| a-3  | a-24 | a-46 | a-67 | a-88  | a-115 | a-135 |
| a-4  | a-25 | a-49 | a-68 | a-90  | a-116 | a-137 |
| a-7  | a-26 | a-50 | a-69 | a-92  | a-117 | a-138 |
| a-8  | a-28 | a-51 | a-70 | a-96  | a-118 | a-139 |
| a-9  | a-29 | a-53 | a-71 | a-97  | a-119 | a-141 |
| a-10 | a-30 | a-54 | a-73 | a-98  | a-120 | a-142 |
| a-11 | a-31 | a-55 | a-75 | a-99  | a-121 | a-143 |
| a-12 | a-32 | a-56 | a-76 | a-100 | a-122 | b-1   |
| a-13 | a-33 | a-57 | a-78 | a-103 | a-123 | b-2   |
| a-14 | a-34 | a-58 | a-79 | a-104 | a-124 | b-3   |
| a-15 | a-35 | a-59 | a-80 | a-105 | a-126 | b-4   |
| a-16 | a-36 | a-60 | a-81 | a-106 | a-127 | b-6   |
| a-18 | a-37 | a-61 | a-82 | a-109 | a-128 |       |
| a-19 | a-38 | a-62 | a-83 | a-110 | a-129 |       |
| a-20 | a-39 | a-63 | a-84 | a-111 | a-131 |       |
| a-21 | a-40 | a-64 | a-85 | a-112 | a-132 |       |

(Test Example 2) Efficacy Test Against *Spodoptera litura*

The emulsion (1) was diluted with water to achieve a concentration of the compound of the present invention of 125 ppm. Cabbage leaves were soaked in the diluted liquid for 30 seconds. These cabbage leaves were then placed in a Petri dish, and five second-instar larvae of *Spodoptera litura* were released into the dish. The Petri dish was placed in a temperature-controlled room at a temperature of 25° C. and a humidity of 60%. Mortality was investigated 6 days after larvae release, and the mortality rate was calculated. The test was repeated.

Efficacy tests against *Spodoptera litura* were conducted for the compounds having the compound numbers shown in Table 5. All of the compounds produced a mortality rate against *Spodoptera litura* of at least 80%.

TABLE 5

| a-1 | a-9  | a-16 | a-23 | a-29 | a-41 | a-64 |
|-----|------|------|------|------|------|------|
| a-2 | a-10 | a-18 | a-24 | a-30 | a-42 | b-2  |
| a-3 | a-11 | a-19 | a-25 | a-34 | a-50 | b-3  |
| a-4 | a-12 | a-20 | a-26 | a-35 | a-54 | b-4  |
| a-7 | a-14 | a-21 | a-27 | a-37 | a-55 | b-6  |
| a-8 | a-15 | a-22 | a-28 | a-39 | a-56 |      |

(Test Example 3) Efficacy Test Against *Plutella xylostella*

The emulsion (I) was diluted with water to achieve a concentration of the compound of the present invention of 125 ppm. Cabbage leaves were soaked in the diluted liquid for 30 seconds. These cabbage leaves were then placed in a Petri dish, and five second-instar larvae of *Plutella xylostella* were released into the dish. The Petri dish was placed in a temperature-controlled room at a temperature of 25° C. and a humidity of 60%. Mortality was investigated 3 days after larvae release, and the mortality rate was calculated. The test was repeated.

Efficacy tests against *Plutella xylostella* were conducted for the compounds having the compound numbers shown in Table 6. All of the compounds produced a mortality rate against *Spodoptera litura* of at least 80%.

TABLE 6

| a-1  | a-22 | a-32 | a-40 | a-54 | a-67 | b-6 |
|------|------|------|------|------|------|-----|
| a-2  | a-23 | a-33 | a-41 | a-55 | a-76 |     |
| a-3  | a-24 | a-34 | a-42 | a-56 | a-78 |     |
| a-4  | a-25 | a-35 | a-49 | a-58 | b-1  |     |
| a-7  | a-26 | a-36 | a-50 | a-64 | b-2  |     |
| a-15 | a-29 | a-37 | a-51 | a-65 | b-3  |     |
| a-21 | a-30 | a-39 | a-53 | a-66 | b-4  |     |

(Test Example 4) Efficacy Test Against *Meloidogyne incognita*

(Clubroot Formation Suppression Test)

The emulsion (I) was diluted with water to achieve a concentration of the compound of the present invention of 125 ppm. A plastic container with a diameter of 5 cm was filled with 7 g of a culture medium, and cucumber seeds were planted. The culture medium was irrigated with 1 ml of the above dilute liquid, and then inoculated with 200 eggs of *Meloidogyne incognita*. The container was then placed in a temperature-controlled room at a temperature of 25° C. and a humidity of 60%, and after 14 days, the clubroot formation suppression ratio (%) relative to an untreated sample was calculated from the number of clubroots formed on the roots of the cucumber plants. The test was repeated.

Clubroot formation suppression ratio (%)=(1−Nt/Nc)×100

Nt: Total number of club roots formed in two treated samples after 14 days

Nc: Total number of club roots formed in two untreated samples after 14 days

Efficacy tests against *Meloidogyne incognita* were conducted for the compounds having the compound numbers shown in Table 7. All of the compounds produced a clubroot formation suppression ratio against *Meloidogyne incognita* of at least 80%.

TABLE 7

| a-1 | a-16 | a-40 | a-59 | a-74 | a-87 | a-102 | a-121 | a-136 |
|---|---|---|---|---|---|---|---|---|
| a-2 | a-22 | a-41 | a-60 | a-75 | a-88 | a-103 | a-122 | a-137 |
| a-3 | a-24 | a-42 | a-61 | a-76 | a-90 | a-109 | a-123 | a-138 |
| a-4 | a-26 | a-49 | a-62 | a-78 | a-91 | a-110 | a-124 | a-139 |
| a-6 | a-28 | a-50 | a-63 | a-79 | a-92 | a-111 | a-126 | a-141 |
| a-7 | a-29 | a-51 | a-64 | a-80 | a-93 | a-112 | a-127 | a-143 |
| a-8 | a-32 | a-53 | a-67 | a-81 | a-95 | a-113 | a-128 | b-4 |
| a-9 | a-34 | a-54 | a-68 | a-82 | a-96 | a-115 | a-129 | b-5 |
| a-10 | a-35 | a-55 | a-69 | a-83 | a-97 | a-116 | a-131 | b-6 |
| a-11 | a-36 | a-56 | a-70 | a-84 | a-98 | a-118 | a-132 | |
| a-14 | a-38 | a-57 | a-71 | a-85 | a-99 | a-119 | a-134 | |
| a-15 | a-39 | a-58 | a-73 | a-86 | a-100 | a-120 | a-135 | |

(Test Example 5) Efficacy Test Against *Meloidogyne incognita* (In Vitro Test)

Two hundred μL of a suspension containing about 50 second-instar larvae (L2) of *Meloidogyne incognita* was dispensed into each well of a 96-well microplate, and 0.2 μL of a 10,000 ppm dimethylsulfoxide solution of the compound of the present invention was injected into each well to achieve a final concentration of 50 ppm. Mortality was investigated after 2 days treatment at 15° C., and the nematode mortality rate was calculated. Observation was performed for 10 seconds, and those individuals that showed no movement in that time were deemed to be dead. The test was repeated.

Efficacy tests against *Meloidogyne incognita* were conducted for the compounds having the compound numbers shown in Table 8. All of the compounds produced a nematode mortality (still) rate against *Meloidogyne incognita* of at least 80%.

TABLE 8

| a-1 | a-17 | a-37 | a-58 | a-76 | a-92 | a-113 | a-131 |
|---|---|---|---|---|---|---|---|
| a-2 | a-18 | a-38 | a-59 | a-78 | a-93 | a-115 | a-132 |
| a-3 | a-22 | a-39 | a-60 | a-79 | a-95 | a-116 | a-134 |
| a-4 | a-24 | a-40 | a-61 | a-80 | a-96 | a-118 | a-135 |
| a-6 | a-25 | a-41 | a-62 | a-81 | a-97 | a-119 | a-136 |
| a-7 | a-26 | a-42 | a-63 | a-82 | a-98 | a-120 | a-137 |
| a-8 | a-28 | a-49 | a-64 | a-83 | a-99 | a-121 | a-138 |
| a-9 | a-29 | a-50 | a-67 | a-84 | a-100 | a-122 | a-139 |
| a-10 | a-30 | a-51 | a-68 | a-85 | a-102 | a-123 | a-141 |
| a-11 | a-32 | a-53 | a-69 | a-86 | a-103 | a-124 | a-143 |
| a-12 | a-33 | a-54 | a-70 | a-87 | a-109 | a-126 | b-1 |
| a-14 | a-34 | a-55 | a-71 | a-88 | a-110 | a-127 | b-4 |
| a-15 | a-35 | a-56 | a-73 | a-90 | a-111 | a-128 | b-5 |
| a-16 | a-36 | a-57 | a-75 | a-91 | a-112 | a-129 | |

(Test Example 6) Efficacy Test Against *Caenorhabditis elegans* (In Vitro Test)

Two hundred μL of a suspension containing about 50 mixed instars of *Caenorhabditis elegans* was dispensed into each well of a 96-well microplate, and 0.2 μL of a 10,000 ppm dimethylsulfoxide solution of the compound of the present invention was injected into each well to achieve a final concentration of 50 ppm. Mortality was investigated after 2 days treatment at 25° C., and the nematode mortality rate was calculated. Observation was performed for 10 seconds, and those individuals that showed no movement in that time were deemed to be dead. The test was repeated.

Efficacy tests against *Caenorhabditis elegans* were conducted for the compounds having the compound numbers shown in Table 9. All of the compounds produced a nematode mortality rate against *Caenorhabditis elegans* of at least 80%.

TABLE 9

| a-1 | a-16 | a-33 | a-53 | a-68 | a-103 | a-118 | a-137 |
|---|---|---|---|---|---|---|---|
| a-2 | a-18 | a-34 | a-54 | a-69 | a-104 | a-119 | a-138 |
| a-3 | a-19 | a-35 | a-55 | a-70 | a-106 | a-120 | a-142 |
| a-4 | a-20 | a-36 | a-56 | a-75 | a-107 | a-121 | a-143 |
| a-6 | a-22 | a-37 | a-57 | a-76 | a-109 | a-122 | b-4 |
| a-7 | a-24 | a-38 | a-58 | a-78 | a-110 | a-123 | b-5 |
| a-8 | a-25 | a-39 | a-60 | a-79 | a-111 | a-124 | b-6 |
| a-9 | a-26 | a-40 | a-61 | a-88 | a-112 | a-126 | |
| a-10 | a-28 | a-41 | a-62 | a-90 | a-113 | a-127 | |
| a-11 | a-29 | a-42 | a-63 | a-93 | a-114 | a-128 | |
| a-12 | a-30 | a-49 | a-64 | a-97 | a-115 | a-129 | |
| a-14 | a-31 | a-50 | a-66 | a-98 | a-116 | a-132 | |
| a-15 | a-32 | a-51 | a-67 | a-99 | a-117 | a-133 | |

(Test Example 7) Efficacy Test Against *Heterodera glycines* (In Vitro Test)

Two hundred μL of a suspension containing about 50 second-instar larvae (L2) of *Heterodera glycines* was dispensed into each well of a 96-well microplate, and 0.2 μL of a 10,000 ppm dimethylsulfoxide solution of the compound of the present invention was injected into each well to achieve a final concentration of 10 ppm. Mortality was investigated after 3 days treatment at 25° C., and the nematode mortality rate was calculated. Observation was performed for 10 seconds, and those individuals that showed no movement in that time were deemed to be dead. The test was repeated.

Efficacy tests against *Heterodera glycines* were conducted for the compounds having the compound numbers shown in Table 10. All of the compounds produced a nematode mortality rate against *Heterodera glycines* of at least 80%.

TABLE 10

| a-2 | a-63 | a-135 |
|---|---|---|
| a-4 | a-76 | a-136 |
| a-15 | a-78 | |
| a-58 | a-134 | |

(Test Example 8) Contact/Ingestion Efficacy Test Against *Aedes aegypti* Larvae

A DMSO solution of the compound of the present invention was diluted with water to obtain a 125 μM dilute solution. Ten first-instar larvae of *Aedes aegypti* were placed in each well of a 96-well microtiter plate, the above dilute liquid was added in a ratio of 1/10, and a test was conducted at a final concentration of 12.5 μM. The samples were incubated in a temperature-controlled room (28° C., 80% RH), and after 48 hours of treatment with the compound, the mortality of the larvae was investigated. The test was repeated.

Contact/ingestion efficacy tests against *Aedes aegypti* larvae were conducted for the compounds having the compound numbers shown in Table 11. All of the compounds produced a mortality rate against *Aedes aegypti* of at least 80%.

TABLE 11

| a-1 | a-9 | a-18 | a-26 | a-34 | a-42 | a-87 |
|---|---|---|---|---|---|---|
| a-2 | a-10 | a-19 | a-28 | a-35 | a-49 | a-88 |
| a-3 | a-11 | a-20 | a-29 | a-36 | a-58 | a-93 |
| a-4 | a-12 | a-22 | a-30 | a-37 | a-60 | a-100 |
| a-6 | a-14 | a-23 | a-31 | a-39 | a-73 | b-1 |

TABLE 11-continued

| a-7 | a-15 | a-24 | a-32 | a-40 | a-76 | b-2 |
| a-8 | a-16 | a-25 | a-33 | a-41 | a-78 | b-3 |

(Test Example 9) Efficacy Tests Against *Ascaridia galli* and *Oesophagostomum* Dentatum Using the gut-welling larval stages of two parasitic worms: namely, the third stage larvae (L3) of *Ascaridia galli*, and the third and fourth stage larvae (L3 and L4 respectively) of *Oesophagostomum* dentatum, the bioactivity of compounds of the present invention were investigated in vitro. When conducting these tests, DMSO solutions of the compounds of the present invention were prepared at various concentrations and incubated in the wells of a 96-well microtiter plate. Subsequently, 20 parasitic worm larvae were inoculated into each well. The bioactivity was determined by inspection under a microscope. The inspection under a microscope included evaluations of the mortality rate, injury, motility, development progression, and neutral red uptake by the larvae compared with a DMSO control. The bioactivity was defined by the minimum effective concentration (MEC), which represents the concentration at which at least one larva dies, is injured, undergoes a change in motility or a change in development progression, or exhibits no neutral red uptake.

Efficacy tests against *Ascaridia galli* and *Oesophagostomum dentatum* were conducted for the compounds having the compound numbers shown in Table 12. All of the compounds exhibited activity against at least one type of target parasitic worm at an MEC of 25 µM or less.

TABLE 12

| a-2  | a-14 | a-25 | a-34 | a-58 | a-93  |
| a-3  | a-15 | a-26 | a-35 | a-60 | a-100 |
| a-7  | a-16 | a-28 | a-36 | a-73 | b-1   |
| a-8  | a-17 | a-29 | a-37 | a-76 |       |
| a-9  | a-21 | a-30 | a-41 | a-78 |       |
| a-10 | a-23 | a-32 | a-42 | a-87 |       |
| a-13 | a-24 | a-33 | a-49 | a-88 |       |

(Test Example 10) Efficacy Test Against *Haemonchus contortus*

Third stage larvae (L3) of *Haemonchus contortus* were collected from the feces of infected sheep, and the bioactivity of compounds of the present invention were investigated in vitro. When conducting this test, DMSO solutions of the compounds of the present invention were prepared at various concentrations and incubated in the wells of a 96-well microtiter plate. Subsequently, 100 parasitic worm larvae were inoculated into each well. The bioactivity was determined by inspection under a microscope. The inspection under a microscope included evaluations of the mortality rate, injury, motility, development progression, and neutral red uptake by the larvae compared with a DMSO control. The bioactivity was defined by the minimum effective concentration (MEC), which represents the concentration at which at least one larva dies, is injured, undergoes a change in motility or a change in development progression, or exhibits no neutral red uptake.

Efficacy tests against *Haemonchus contortus* were conducted for the compounds having the compound numbers shown in Table 13. All of the compounds exhibited activity against L3 larvae of *Haemonchus contortus* at an MEC of 25 µM or less.

TABLE 13

| a-49 | a-76 | a-93  |
| a-58 | a-78 | a-100 |
| a-60 | a-87 |       |
| a-73 | a-88 |       |

(Test Example 11) Efficacy Test Against *Dirofilaria immitis*

Using the microfilarial stage and the fourth stage larvae (Mf and L4 respectively) of *Dirofilaria immitis*, the bioactivity of compounds of the present invention were investigated in vitro. The Mf was collected from the blood of infected dogs, and 500 microfilariae were inoculated into each well of a 96-well microtiter plate. The L4 larvae was obtained by allowing L3 larvae collected from infected mosquitoes to undergo a single molt, and 10 of these L4 larvae were inoculated into each well. Subsequently, a 10 mM DMSO solution of the compound of the present invention was prepared at various concentrations and added to each well in a ratio of 1/1,000, and a test was then conducted at a final concentration of 10 µM. Incubation was performed at 37° C. in an environment containing 5% carbon dioxide, and 72 hours after treatment with the compound, the mortality and growth inhibition were determined. The test was repeated.

An efficacy test against *Dirofilaria immitis* was conducted for the compound having the compound number a-26. At 10 µM, this compound exhibited a mortality rate or growth inhibition rate of at least 90% against both the Mf and L4 growth stages.

Based on the fact that compounds selected randomly from the compounds of the present invention all exhibited the types of effects described above, it is evident that the compounds of the present invention, including those compounds not exemplified above, have pest control effects, and in particular, insecticidal, miticidal and nematicidal effects or the like.

INDUSTRIAL APPLICABILITY

The present invention can provide a sufonylaminobenzamide compound that has pest control activity, and in particular, has excellent insecticidal, miticidal and/or nematicidal activity, exhibits excellent safety, and can be synthesized favorably on an industrial scale, and can also provide a pest control agent that contains this compound as an active constituent.

The invention claimed is:

1. A compound represented by formula (I) or a salt thereof:

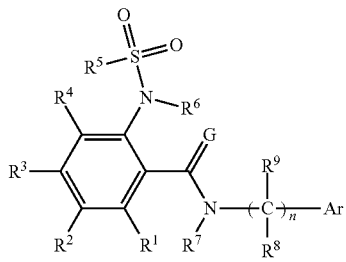

wherein in formula (I):

$R^1$, $R^2$, $R^4$, $R^6$ and $R^7$ each independently represent a hydrogen atom;

$R^3$ represents a substituted C1 to C6 alkyl group;

$R^5$ represents a trifluoromethyl group;

G represents an oxygen atom or a sulfur atom;

n represents 0 or 1;

$R^8$ and $R^9$ each independently represent a hydrogen atom, or an unsubstituted or substituted C1 to C6 alkyl group; and Ar represents an unsubstituted or substituted C6 to C10 aryl group, wherein the substituent on the C6 to C10 aryl group for Ar is selected from the group consisting of halogeno group, C1 to C6 alkyl group, C1 to C6 haloalkyl group, C1 to C6 alkoxy group, C1 to C6 haloalkoxy group, a carboxyl group, C1 to C6 alkylcarbonyl group, C1 to C6 alkylcarbonylamino group, C1 to C6 alkoxycarbonyl group, unsubstituted or C1 to C6 alkyl-substituted 5-membered heteroaryl group, a 4,5-dihydrooxazol-2-yl group, 6-membered heteroaryl group, C1 to C6 alkoxyimino C1 to C6 alkyl group, a cyano group, a nitro group, and a pentafluorosulfanyl group.

2. A pest control agent comprising at least one substance selected from the group consisting of the compound according to claim 1 and salts thereof as an active constituent.

3. A nematicide comprising at least one substance selected from the group consisting of the compound according to claim 1 and salts thereof as an active constituent.

* * * * *